US011850741B2

(12) United States Patent
Masuda et al.

(10) Patent No.: US 11,850,741 B2
(45) Date of Patent: Dec. 26, 2023

(54) CONTROL DEVICE, CONTROL METHOD, AND MASTER-SLAVE SYSTEM

(71) Applicant: SONY CORPORATION, Tokyo (JP)

(72) Inventors: Hiromasa Masuda, Tokyo (JP); Yuki Itotani, Tokyo (JP)

(73) Assignee: SONY CORPORATION, Tokyo (JP)

( * ) Notice: Subject to any disclaimer, the term of this patent is extended or adjusted under 35 U.S.C. 154(b) by 840 days.

(21) Appl. No.: 16/628,285

(22) PCT Filed: May 23, 2018

(86) PCT No.: PCT/JP2018/019872
§ 371 (c)(1),
(2) Date: Jan. 3, 2020

(87) PCT Pub. No.: WO2019/012812
PCT Pub. Date: Jan. 17, 2019

(65) Prior Publication Data
US 2020/0214779 A1 Jul. 9, 2020

(30) Foreign Application Priority Data

Jul. 12, 2017 (JP) .................................. 2017-135995

(51) Int. Cl.
*B25J 3/00* (2006.01)
*A61B 34/37* (2016.01)
*A61B 34/00* (2016.01)
*A61B 34/30* (2016.01)

(52) U.S. Cl.
CPC ................. *B25J 3/00* (2013.01); *A61B 34/25* (2016.02); *A61B 34/37* (2016.02); *A61B 2034/302* (2016.02)

(58) Field of Classification Search
CPC .... B25J 3/00; B25J 3/04; B25J 9/1689; A61B 34/25; A61B 34/37; A61B 2034/302; A61B 2090/066; G05B 2219/1215; G05B 19/056
See application file for complete search history.

(56) References Cited

U.S. PATENT DOCUMENTS 5,021,969 A    6/1991   Okamura et al.
6,216,056 B1   4/2001   Ito et al.
(Continued)

FOREIGN PATENT DOCUMENTS

CN    105555222 A    5/2016
DE    69716018 T2    2/2003
(Continued)

OTHER PUBLICATIONS

Office Action for JP Patent Application No. 2019-528961, dated Apr. 5, 2022, 06 pages of English Translation and 05 pages of Office Action.
(Continued)

*Primary Examiner* — Richard G Louis
(74) *Attorney, Agent, or Firm* — CHIP LAW GROUP

(57) ABSTRACT

A control device and a control method of a master-slave system and the master-slave system are provided. A control device, which controls an operation of a master-slave system, includes a control unit that applies, to a control system of the master-slave system, a restraint force corresponding to an operation in a desired translational or rotational direction by the master. The control unit applies, to the control system, the restraint force according to a difference between a current position or posture of the master and a reference value of a position or posture to be restrained. The control system controls the master-slave system, for example, by a bilateral control method or a unilateral control method.

16 Claims, 21 Drawing Sheets

(56) References Cited

U.S. PATENT DOCUMENTS

| | | | | |
|---|---|---|---|---|
| 2003/0097060 A1* | 5/2003 | Yanof | ............... | A61B 34/76 600/424 |
| 2003/0195664 A1* | 10/2003 | Nowlin | ............ | A61B 34/37 318/568.11 |
| 2013/0024024 A1* | 1/2013 | Namiki | ............ | A61B 1/00149 700/245 |
| 2015/0250547 A1 | 9/2015 | Fukushima et al. | | |
| 2015/0313679 A1 | 11/2015 | Fukushima et al. | | |
| 2017/0079729 A1 | 3/2017 | Fukushima et al. | | |
| 2017/0319283 A1* | 11/2017 | Suresh | ............ | A61B 34/25 |

FOREIGN PATENT DOCUMENTS

| | | |
|---|---|---|
| EP | 0849053 A1 | 6/1998 |
| EP | 3037222 A1 | 6/2016 |
| JP | 61-252080 A | 11/1986 |
| JP | 01-240286 A | 9/1989 |
| JP | 02-059280 A | 2/1990 |
| JP | 10-230489 A | 9/1998 |
| JP | 2003-340752 A | 12/2003 |
| JP | 2015-508682 A | 3/2015 |
| JP | 2015-527906 A | 9/2015 |
| JP | 2018-057934 A | 4/2018 |
| WO | 2015/046081 A1 | 4/2015 |
| WO | 2016/132399 A1 | 8/2016 |

OTHER PUBLICATIONS

International Search Report and Written Opinion of PCT Application No. PCT/JP2018/019872, dated Aug. 7, 2018, 10 pages of ISRWO.

* cited by examiner

ROBOT SYSTEM 1

CONTROL DEVICE, CONTROL METHOD, AND MASTER-SLAVE SYSTEM

CROSS REFERENCE TO RELATED APPLICATIONS

This application is a U.S. National Phase of International Patent Application No. PCT/JP2018/019872 filed on May 23, 2018, which claims priority benefit of Japanese Patent Application No. JP 2017-135995 filed in the Japan Patent Office on Jul. 12, 2017. Each of the above-referenced applications is hereby incorporated herein by reference in its entirety.

TECHNICAL FIELD

The technology disclosed herein relates to a master-slave system, and particularly, to a control device and a control method of a master-slave robot and a master-slave system.

BACKGROUND ART

In recent years, a large number of master-slave robots have been developed (for example, refer to Patent Document 1). This type of robot is used not only in the medical field but also in remote control of works under extreme environments.

Regarding a master-slave robot, it is generally important that a behavior on a side of a master by an operator is reproduced by a behavior on a side of a slave at high accuracy. However, tasks performed by the operator include tasks having a possibility to improve operation accuracy and shorten a task processing time not only by simply reproducing the behavior on the side of the master by the operator but also supporting or assisting the operator by a side of a robot. This is one of advantages of performing the tasks by humans by using the master-slave robots.

For example, a system in which a robot automatically performs subtasks that require accuracy during surgery has been provided (for example, refer to Patent Document 2). According to this type of system, by tracking a subject and a surgical instrument by using sensor information, it is possible for a robot to automatically perform the formulated subtasks and assist a user who is the operator.

CITATION LIST

Patent Document

Patent Document 1: PCT Japanese Translation Patent Publication No. 2015-508682
Patent Document 2: PCT Japanese Translation Patent Publication No. 2015-527906

SUMMARY OF THE INVENTION

Problems to be Solved by the Invention

An object of the technology disclosed herein is to provide a control device and a control method of a master-slave system and a master-slave system.

Solutions to Problems

A first aspect of the technology disclosed herein is a control device that controls an operation of a master-slave system, including a control unit that applies, to a control system of the master-slave system, a restraint force corresponding to an operation in a desired translational or rotational direction by the master.

The control unit applies, to the control system, the restraint force according to a difference between a current position or posture of the master and a reference value of a position or posture to be restrained. Furthermore, the control system controls the master-slave system, for example, by a bilateral control method or a unilateral control method.

Furthermore, a second aspect of the technology disclosed herein is a control method for controlling an operation of a master-slave system, including a control step of applying, to a control system of the master-slave system, a restraint force corresponding to an operation in a desired translational or rotational direction by the master.

Furthermore, a third aspect of the technology disclosed herein is a master-slave system including a master, a slave, and a control unit that controls an operation of the slave by the master, in which the control unit applies a restraint force corresponding to an operation in a desired translational or rotational direction by the master.

However, "system" here indicates a plurality of devices (or functional module for realizing specific function) that is logically collected, and it does not matter whether or not the devices or functional modules are provided in a single housing. The master includes, for example, a support arm unit having a parallel link structure and a grip portion disposed on a side of a distal end of the support arm unit. Furthermore, the slave includes a detection unit that detects an external force, and the master includes a force presentation unit that presents a force based on a detection result by the detection unit. Furthermore, the slave includes a multi-link arm, and a medical unit is attached at a front end of the multi-link arm.

Effects of the Invention

According to the technology disclosed herein, a control device and a control method of a master-slave system and a master-slave system can be provided.

Note that the effects described herein are only exemplary, and the effect of the present invention is not limited to those. Furthermore, there is a case where the present invention further has an additional effect other than the effects described above.

Other purpose, characteristics, and advantages of the technology disclosed herein would be obvious by the detailed description based on the embodiment described later and the attached drawings.

MODE FOR CARRYING OUT THE INVENTION

Figure 1:
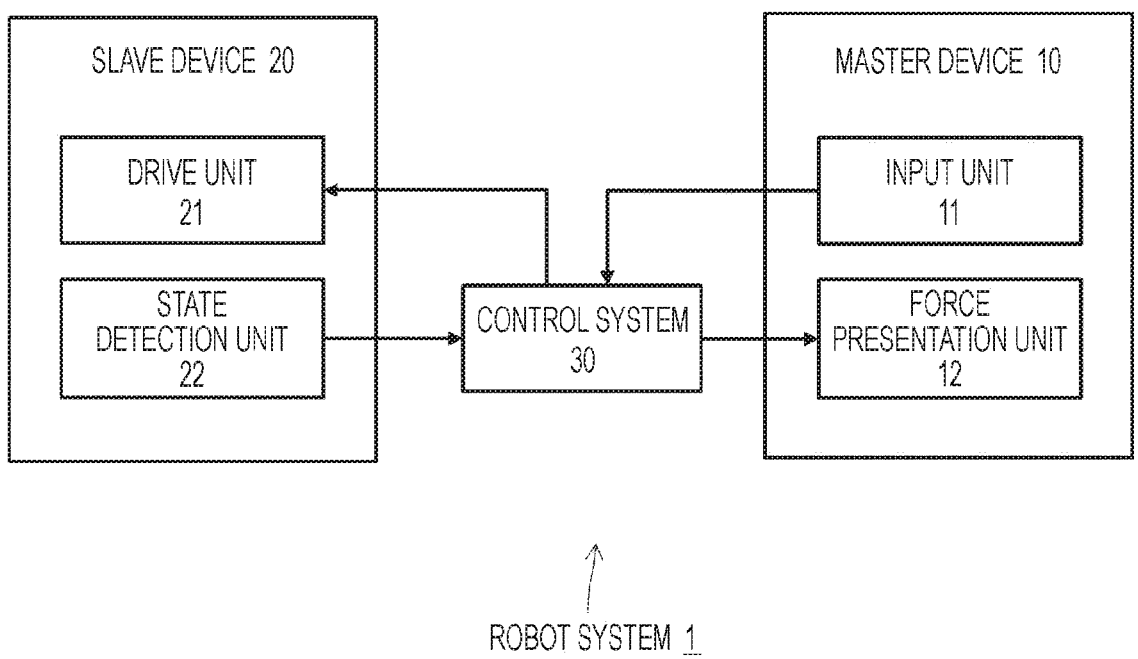
FIG. 1 is a diagram of an exemplary functional configuration of a master-slave type robot system 1.

Hereinafter, an embodiment of the technology disclosed herein will be described in detail with reference to the drawings.

For example, a system in which a robot automatically performs some subtasks (suture and the like) that require accuracy during surgery has been provided (as described above). However, this type of existing system only provides automation of some formalized subtasks.

For example, there is a case where it is desired to accurately move a surgical instrument in one axial direction during surgery. Even if a user tries to operate the surgical instrument in one axial direction on a side of a master device, a case often occurs where the surgical instrument shifts in another-axis direction. When the slave device reproduces such an inaccurate input operation on the side of the master device, there is a possibility to invade an affected part.

In other words, it can be said that an existing system is flawed to support or assist a master-slave behavior of the user in a general behavior including a translational motion and a rotational motion and a subtask that is not formulated. Furthermore, the applicant considers that it is necessary to sufficiently consider safety, when the robot automatically performs the task, such as a damage, an accident, and the like caused by an unexpected collision (by robot or environment) in the task environment.

Therefore, here, a master-slave robot will be proposed below that can support or assist the operator with high accuracy in a general behavior including an arbitrary translational motion and rotational motion without limiting to the formulated subtasks.

Furthermore, here, technology regarding an operation user interface (UI) associated with the master-slave robot that supports or assists the operator and a presentation UI that presents information such as an operation state will be also proposed.

The technology disclosed herein can be suitably applied to, for example, a bilateral control system. The bilateral control here indicates a control method in which the master operates the slave, and at the same time, the state of the slave is fed back to the master, under master-slave control. According to the bilateral control, it is possible to present a force to the user who operates the master. An ideal bilateral control system can simultaneously match the positions and forces of the master and the slave. Incidentally, a control method in which a state of the slave (position and force of slave) is not fed back to the master under the master-slave control is unilateral control. As will be described later, the technology disclosed herein can be also applied to a unilateral control system.

According to the technology disclosed herein, it is possible to support or assist an arbitrary translational motion and rotational motion while continuously behaving the master-slave robot in a bilateral control mode, and it is not necessary to shift control modes such as a mode for performing a master-slave behavior, a behavior mode for assisting the operator as performing autonomous behavior, and the like.

Furthermore, according to the master-slave robot to which the technology disclosed herein is applied, the operator who operates the master can recognize the collision and the like in the task environment on the side of the slave. Therefore, safety is also enhanced.

In FIG. 1, an exemplary functional configuration of a master-slave type robot system 1 to which the technology disclosed herein can be applied is schematically illustrated. The illustrated robot system 1 is a medical robot system that performs an endoscopic surgical operation, for example, an abdominal cavity or a chest cavity. In response to an instruction input by a user on a master side via an input device such as a controller and the like, an arm on a side of a slave and an end effector such as a medical instrument attached to the arm are driven, and various treatments are performed on a patient's surgical site by the medical instrument.

The illustrated robot system 1 includes a master device 10, a slave device 20, and a control system 30 that drives the slave device 20 in response to an instruction by a user input via the master device 10. When the user operates the master device 10, an operation instruction to the slave device 20 is transmitted by a wired or wireless communication unit through the control system 30, and the slave device 20 is operated.

The master device 10 includes an input unit 11 used to perform an input operation by a user such as an operator and a force presentation unit 12 that presents a force to the user who is operating the input unit 11.

The input unit 11 may include, for example, an input mechanism such as a lever, a grip, a button, a jog dial, a tact switch, a foot pedal switch, or the like. However, a specific configuration of the input unit 11 is not limited to the above, and it is possible to use various known configurations that may be provided in an input device of a general master-slave type robot system.

Furthermore, the force presentation unit 12 includes, for example, a servo motor that drives the lever, the grip, and the like included in the input unit 11, and in addition, a servo motor that drives an arm for instructing the input unit 11, and the like. The force presentation unit 12 represents a force acting on the medical instrument to the user by driving the lever, the arm, and the like included in the input unit 11, for example, so as to give a resistance to the operation on the input unit 11 by the user according to a force acting on the medical instrument on the side of the slave device 20.

The slave device 20 includes a support arm device that includes an arm in which a plurality of links is rotatably coupled to each other by joint portions, a drive unit 21 that drives the arm of the support arm device and the medical instrument at the front end, and a state detection unit 22 that detects a state of the support arm device. Note that it is assumed that a medical instrument such as a forceps be attached at the front end (end effector) of the arm. Furthermore, instead of the forceps, another medical tool such as tweezers or a cutting tool that has contact with a patient during a surgical operation and an imaging device such as an endoscope or a microscope may be attached.

For convenience, illustration of the support arm device is omitted in FIG. 1. The support arm device has six degrees of freedom in a position and a posture that change a position and a direction of the end effector of the arm in a three-dimensional space and one degree of freedom for gripping an object by the forceps attached at the front end of the arm. Details of the support arm device will be described later.

For example, the drive unit 21 corresponds to a motor that is provided in each joint portion of the arm of the support arm device and is used to rotate and drive each joint portion. Furthermore, in a case where the medical tool such as the forceps attached at the front end of the arm has a driving portion, the drive unit 21 corresponds to a motor for making the driving portion behave. By driving the motor according to a control amount calculated by the control system 30, the arm and the medical instrument behave as instructed by the user via the master device 10.

The state detection unit 22 includes, for example, a force sensor (torque sensor) provided in each joint portion of the arm of the support arm device, an encoder, and the like and detects a state of the arm. The force sensor can detect a force (torque) acting on each joint portion. Furthermore, the encoder can detect a rotation angle of each joint portion.

The control system 30 realizes drive control of the support arm device on the side of the slave device 20 and transmission of information regarding force presentation to the side of the master device 10 between the master device 10 and the slave device 20. However, a part of or all of the functions of the control system 30 may be provided at least in one of the slave device 20 or the master device 10. For example, a central processing unit (CPU) (not illustrated) of at least one of the master device 10 or the slave device 20 functions as the control system 30. Alternatively, the respective CPUs of the master device 10 and the slave device 20 function as the control system 30 in cooperation with each other. A specific configuration of the control system 30 will be described later.

Note that, in FIG. 1, only the configurations that are particularly necessary for describing the embodiment according to the technology disclosed herein are illustrated. The robot system 1 may include other functional blocks included in a general master-slave type robot system, in addition to the illustrated functional blocks. Since various known configurations can be applied to the configuration that is not illustrated, detailed description thereof will be omitted in the present specification.

When the side of the master device 10 drives and controls the slave device 20, information indicating the instruction to drive the arm of the support arm device input by the user via the input unit 11 of the master device 10 is transmitted to the control system 30. In a case where, on the side of the slave device 20, the medical instrument has a driving portion as a robot forceps described above, information indicating an instruction to drive the medical instrument input via the input unit 11 may be also input from the master device 10 to the control system 30.

The control system 30 calculates the control amount used to drive the arm of the support arm device on the side of the slave device 20 on the basis of the instruction input from the user via the input unit 11. For example, in a case where the support arm device is driven and controlled by force control, the control system 30 calculates a torque, as the control amount, required to be generated in each joint portion necessary for realizing a desired behavior of the arm instructed by the user. Alternatively, in a case where the support arm device is driven and controlled by positional control, the control system 30 calculates a rotation angle of each joint portion, as the control amount, necessary for realizing the desired behavior of the arm instructed by the user. Furthermore, in a case where the medical instrument included in the arm includes a driving portion, the control system 30 calculates a control amount for driving the medical instrument.

In the present embodiment, as a drive and control method, it is assumed to employ a bilateral control method for simultaneously controlling the positions and forces of the master device 10 and the slave device 20. However, this point will be described in detail later.

Information regarding the control amount calculated by the control system 30 is transmitted to the drive unit 21 on the side of the slave device 20. The drive unit 21 drives each joint portion of the arm according to the control amount calculated by the control system 30 so that the arm behaves as instructed by the user via the input unit 11. Furthermore, in a case where the medical instrument attached at the front end of the arm includes a driving portion, a motor that makes the driving portion behave drives according to the control amount calculated by the control system 30 so as to make the medical instrument behave as instructed by the user via the input unit 11.

Furthermore, while the arm and the medical instrument at the front end of the arm are behaving, the state detection unit 22 including a torque sensor, an encoder, and the like detects the force (torque) acting on each joint portion of the arm, the rotation angle of each joint portion, and the like as a state of the support arm device. The information indicating the state of the arm detected by the state detection unit 22 is transmitted to the control system 30. The control system 30 sequentially grasps the current state of the arm on the basis of the information and calculates the control amount on the basis of the grasped current state of the arm.

Here, it is estimated that the force acting on each joint portion detected by the force sensor reflects the force acting on the medical instrument attached at the front end of the arm. The control system 30 extracts a component of the force acting on the medical instrument from among the force acting on each joint portion detected by the force sensor and transmits the extracted component to the force presentation unit 12 of the master device 10. The force presentation unit 12 presents the force acting on the medical instrument to the operator according to the force acting on the medical instrument. For example, the lever and the like included in the input unit 11 is driven so as to give a resistance to the operation of the input unit 11 by the user who is the operator. In this way, the robot system 1 according to the present embodiment has a function for detecting the force acting on the medical instrument and feeding back the force to the operator. This can contribute to realize minimum invasive treatment using an endoscope.

Figure 2:
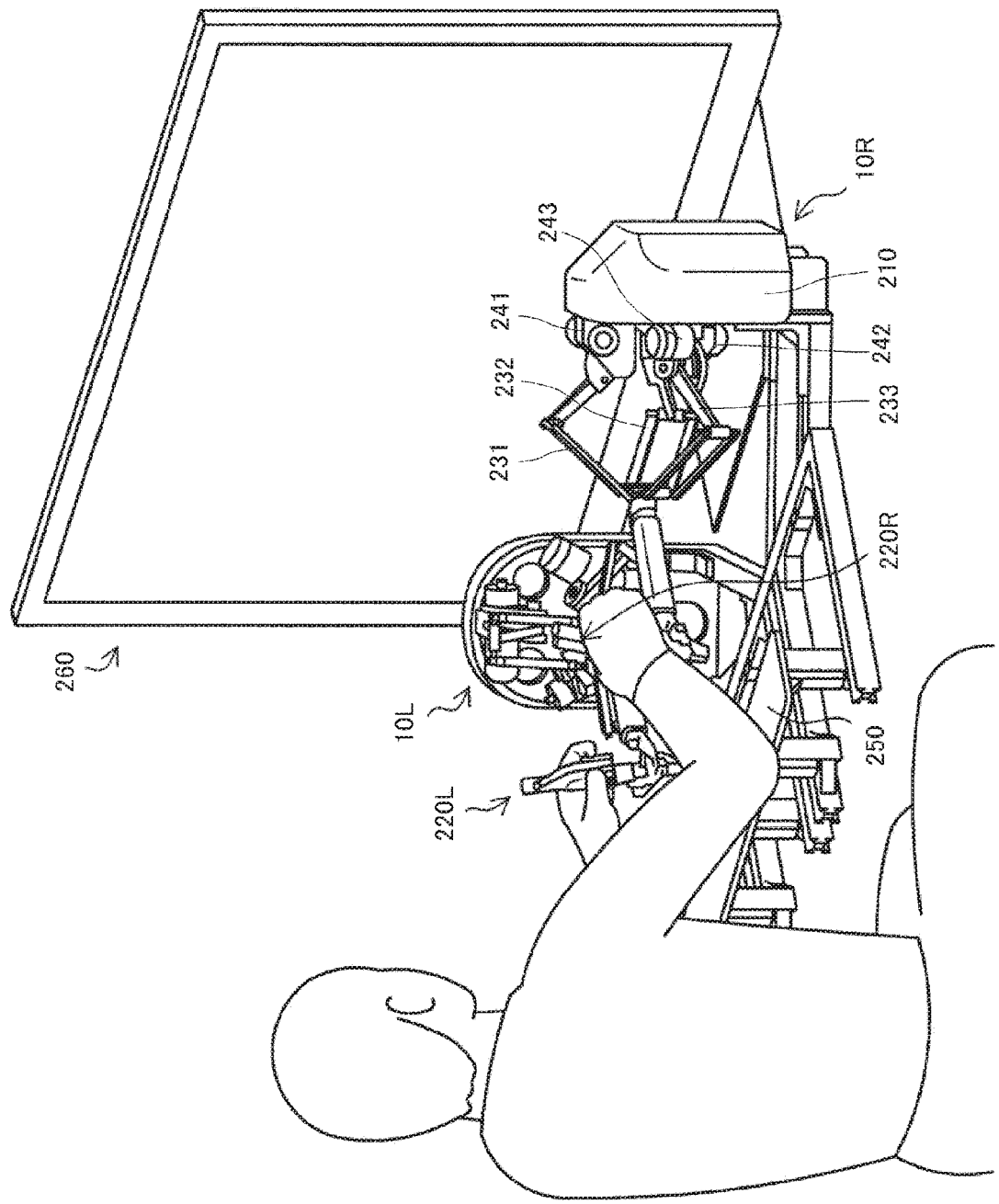
FIG. 2 is a diagram of an exemplary configuration of a master device 10.

In FIG. 2, an exemplary configuration of the master device 10 is illustrated. In the illustrated example, two master devices 10R and 10L respectively for right and left hands are provided. However, it is not necessarily necessary to prepare the master devices 10 for right and left hands in order to remotely operate the slave device 20, and it is sufficient to mount only one of the master devices 10 for right and left hands. Alternatively, the two master devices 10R and 10L for right and left hands may simultaneously and respectively operate two slave devices in total. Hereinafter, the description will be made as mainly focusing on the master device 10R for the right hand. However, it should be understood that the master device 10L for the left hand has a similar configuration. The master device 10 includes a main body 210, a grip portion 220, a support arm unit that supports the grip portion 220.

The support arm unit is a robot that has a delta-type parallel link structure including three link portions 231, 232, and 233 of which a side of a distal end is coupled. That is, the support arm unit has a three-axis translation structure using a parallel link mechanism and can determine a movement at one point in the three-dimensional space. A side of the base end of each of the link portions 231, 232, and 233 is rotatably coupled to the main body 210. The main body 210 includes motors (for example, servo motor) 241, 242, and 243 respectively drives coupling portions to the link portions 231, 232, and 233. Furthermore, in each coupling portion between the main body 210 and each of the link portions 231, 232, and 233, the encoder (not illustrated) that detects the rotation angle of each of the link portions 231, 232, and 233 to the main body 210 and the torque sensor (not illustrated) that detects a torque generated in each of the link portions 231, 232, and 233 are disposed. Then, a front end of each of the link portions 231, 232, and 223 is coupled to the grip portion 220.

Here, each of the link portions 231, 232, and 233 includes a drive link that is driven by each of the motors 241, 242, and 243 and a passive link that is attached to the drive link via the joint portion. The user can grip the grip portion 220 and displace the grip portion 220 to an arbitrary position and posture in the three-dimensional space. Furthermore, the user can grip and operate the grip portion 220 at an arbitrary position in the three-dimensional space. Therefore, the illustrated master device 10 has six degrees of freedom in the position and the posture in the three-axis direction of the grip portion 220 at the front end and one degree of freedom of the grip of the grip 220.

As illustrated in FIG. 2, the user can place both arms or both elbows on a support base 250 and grip grip portions 220R and 220L respectively by the right and left hands so as to work. Furthermore, a monitor 260 is installed in front of the user. For example, in a case where a camera is incorporated into the end effector such as the forceps attached to the slave device 20 (or in a case where end effector is endoscopic device), a captured image of a surgical field may be displayed on a screen of the monitor 260.

Therefore, the user can operate the operation grip portions 220R and 220L while viewing the monitor 260 on which the surgical field is displayed. Then, by displacing the position and the direction of each of the grip portions 220R and 220L, the user can remotely operate the position or the direction of the surgical instrument such as the forceps attached to the slave device 20 and perform a behavior for gripping the forceps.

The grip portions 220R and 220L correspond to the input unit 11 of the master device 10 in FIG. 1. The master device 10 may further include a jog dial and a tact switch disposed on the grip portion 220 and a foot pedal switch (not illustrated) separated from the grip portion 220 as the input units 11. While gripping and moving the grip portion 220 by hand, the user can operate the jog dial and the tact switch with fingertips. Furthermore, even in a case where both hands are used to operate the grip portions 220R and 220L, the user can perform a further input operation by stepping on the foot pedal switch with foot.

Furthermore, by synchronously driving the motors 241, 242, and 243, a translational force can be presented to the user who is gripping the grip portion 220. For example, when the surgical instrument is displaced by the side of the slave device 20, it is possible to present the translational force acting on the surgical instrument to the user by driving each of the motors 241, 242, and 243 according to an acting force of the end effector (surgical instrument) detected by the state detection unit 22.

Note that, in the present embodiment, it is assumed that the grip portion 220 further include state detection means that detects whether the user is in a "holding state" in which the user grips or holds the grip portion 220 or in a "non-holding state" in which the user does not hold the grip portion 220. The state detection means can include, for example, a force sensor that detects a grip force added to the grip portion 220. The state detection means may determine a state where the force sensor detects an external force equal to or more than a predetermined value as the "holding state" and may determine a state as the "non-holding state" when the external force is less than the predetermined value. Alternatively, the state detection means can include a pressure sensor, a human sensor, or the like that senses a fingertip of the user having contact with the grip portion 220. The non-holding state is a state where the hand of the user is separated from the grip portion 220, and it can be said that the non-holding state is a state where the grip portion 220 is out of the operation by the user.

Furthermore, in the present embodiment, the grip portion 220 is not only receiving the grip operation by the user (or can be operated in parallel to grip operation), and it is assumed that the grip portion 220 include other input means such as a jog dial or a tact switch.

As illustrated in FIG. 2, in an exemplary configuration of the master device 10 including the left grip portion 220L and the right grip portion 220R, the state detection means and the input means described above are basically included in each of the left and right grip portions 220. However, a configuration in which the state detection means and the input means are included in one of the grip portions 220 is assumed.

Furthermore, it is possible to removably attach the grip portion 220 to the main body 210 (or support arm unit) of the master device 10 and to selectively use a grip portion from a plurality of types of grip portions in the single master device 10. There is a case where a movable range of the master device 10 changes depending on the type of the attached grip portion. For example, each attachable grip portion may have identification information (ID), and the main body 210 or the control system 30 may recognize the type of the attached grip portion by reading the ID of the grip portion attached to the master device 10.

Figure 3:
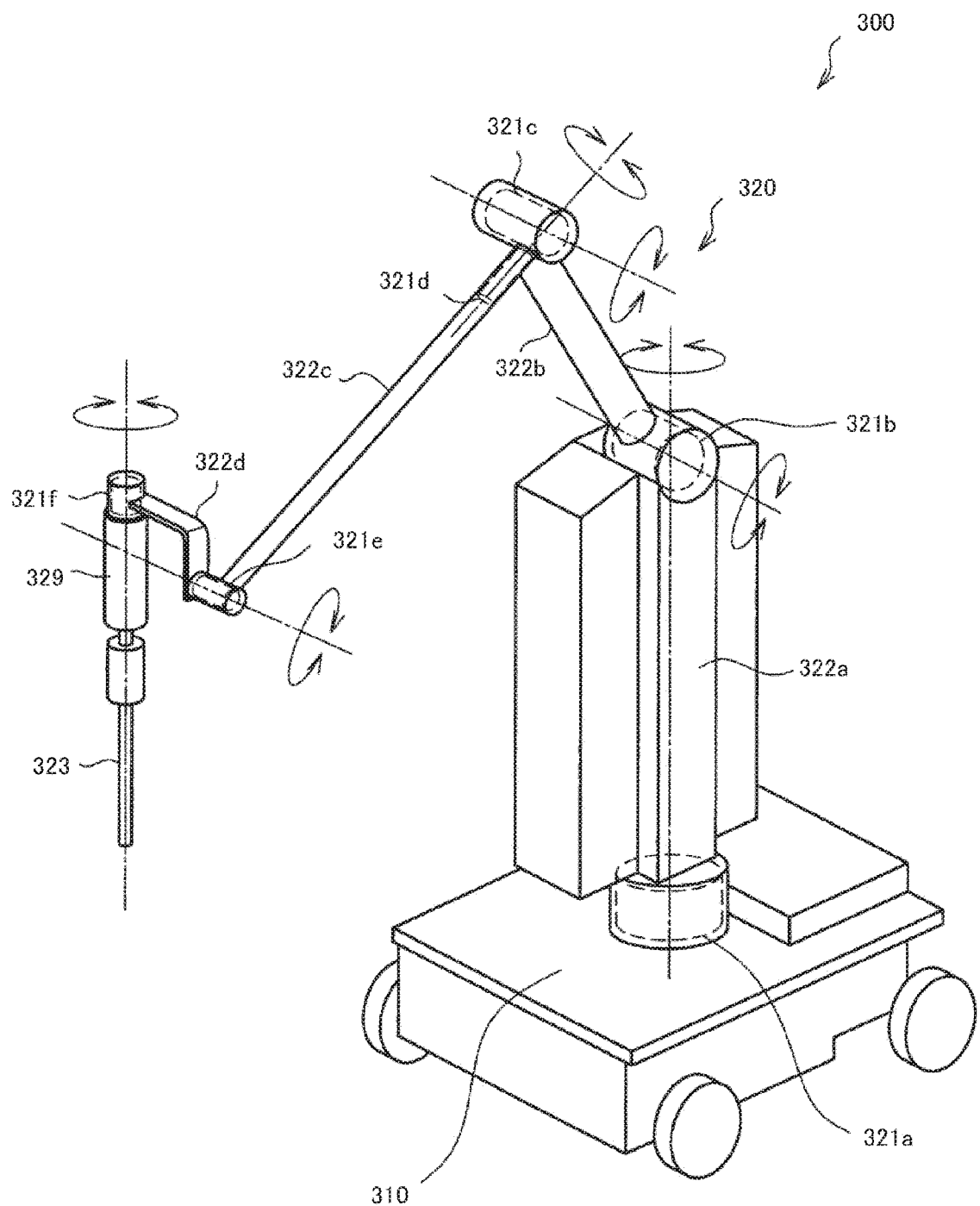
FIG. 3 is a diagram of an exemplary configuration of a slave device 20.

In FIG. 3, an exemplary configuration of a support arm device 300 that is one of the components of the slave device 20 is illustrated. The illustrated support arm device 300 is a medical robot that supports a medical instrument such as a forceps at the time of surgery and includes a base 310 and an arm 320.

The base 310 is a base of the support arm device 300. In the base 310, a control substrate and a microcomputer on which a processor such as a CPU and a digital signal processor (DSP) and a storage element such as a memory are mounted are housed. For example, the control system 30 may be housed in the base 310.

The arm 320 is extended from the base 310. Two pairs of casters are provided on a bottom surface of the base 310. The support arm device 300 has contact with a floor surface via the casters and can move on the floor surface by rotation of the casters. However, the support arm device 300 is not limited to the above configuration. For example, the support arm device 300 may have a suspension structure in which the base 310 is not provided and the arm 320 is directly attached to a ceiling or a wall surface of an operating room.

The arm 320 includes a plurality of joint portions 321a, 321b, 321c, 321d, 321e, and 321f, a plurality of links 322a, 322b, 322c, and 322d that are rotatably coupled to each other by the joint portions 321a to 321e, and a holding unit 329 that is rotatably provided at the front end of the arm 320 via the joint portion 321f. Furthermore, the holding unit 329 holds various medical instruments. In the illustrated example, a forceps 323 is attached to the holding unit 329.

The links 322a to 322c are bar-like members, one end of the link 322a is coupled to the base 310 via the joint portion 321a, and another end of the link 322a is coupled to one end of the link 322b via the joint portion 321b. Moreover, another end of the link 322b is coupled to one end of the link 322c via the joint portions 321c and 321d. Moreover, another end of the link 322c is coupled to one end of the link 322d having a substantially L-like shape via the joint portion 321e, and another end of the link 322d is coupled to the holding unit 329 that holds the forceps 323 via the joint portion 321f. In this way, the ends of the plurality of links 322a to 322d are rotatably coupled to each other via the joint portions 321a to 321f with the base 310 as a fulcrum so that an arm-like shape extending from the base 310 is formed.

In FIG. 3, for easy description, illustration of a specific shape of the forceps 323 is omitted, and the forceps 323 is simply illustrated as a bar-like member. However, in actual, the end effector for performing treatments such as to grip or cut body tissue of a patient is provided at the front end of the forceps 323. When surgery is performed, positions and postures of the arm 320 and the forceps 323 are controlled so that the forceps 323 takes a desired position and posture with respect to the body tissue of the patient.

An actuator is provided in each of the joint portions 321a to 321f. The actuator corresponds to the drive unit 21 in FIG. 1. By driving the actuator, each of the joint portions 321a to 321f can be rotated around the rotation axis. The actuator includes, for example, a motor, an encoder, a torque sensor, and the like. The encoder and the torque sensor correspond to the state detection unit 22 in FIG. 1.

By controlling the drive of the actuator of each of the joint portions 321a to 321f, for example, the arm 320 can be extended or contracted (folded). At this time, the control system 30 may calculate the control amount of the motor of each actuator on the basis of the state of each of the joint portions 321a to 321f detected by the state detection unit 22 such as the encoder, the torque sensor, or the like of the actuator.

In the example illustrated in FIG. 3, the support arm device 300 realizes six degrees of freedom of the position and the posture of the forceps 323 at the front end by driving the arm 320 including the six joint portions 321a to 321f and further has one degree of freedom for the forceps 323 to grip an object. By configuring the arm 320 to have six degrees of freedom, the forceps 323 can be freely moved in the movable range of the arm 320. With this structure, the forceps 323 can be inserted into the patient (abdominal cavity and chest cavity) from various angles, and the degree of freedom at the time of operating the forceps 323 is improved.

However, the configuration of the arm 320 is not limited to the example illustrated in FIG. 3. The number and arrangement of the joint portions 321a to 321f and the links 322a to 322d, directions of drive shafts of the joint portions 321a to 321f, and the like may be appropriately set so that the arm 320 has a desired degree of freedom. In short, the arm 320 having the degree of freedom equal to or more than six degrees of freedom may be appropriately formed in consideration of the degree of freedom of the position and the posture, a mechanical structure, and the like of the forceps 323.

When the arm 320 is behaved, the user issues an instruction to the support arm device 300 via the input unit 11 on the side of the master device 10. A signal indicating the instruction input via the input device is transmitted to the control system 30.

The control system 30 calculates the control amount of the motor of the actuator of each of the joint portions 321a to 321f in response to the instruction on the basis of the state of each of the joint portions 321a to 321f detected by the encoder and the torque sensor of the actuator of each of the joint portions 321a to 321f. By driving the motor of each actuator according to the calculated control amount, the arm 320 behaves according to the instruction of the user.

Furthermore, in a case where the forceps 323 includes the driving portion, similarly, the control system 30 calculates the control amount of the motor used to make the driving portion behave on the basis of the instruction input via the input unit 11. By driving the motor according to the calculated control amount, the forceps 323 behaves according to the instruction of the user.

Note that it is possible to configure the end effector of the slave device 20 to be removable from the holding unit 329 and to be selectively used by exchanging the end effector with the plurality of types of surgical instruments other than the forceps 323. There is a case where the movable range of the slave device 20 changes depending on the type of the attached surgical instrument. For example, each attachable surgical instrument may have the identification information (ID), and the main body of the slave device 20 or the control system 30 may recognize the type by reading the ID of the surgical instrument attached to the slave device 20.

Regarding the master-slave robot system 1 according to the present embodiment, it is assumed to form a bilateral control system. As a bilateral control method, for example, a position-symmetric type, a force-feedback type, and a 4CH type can be exemplified.

Figure 4:
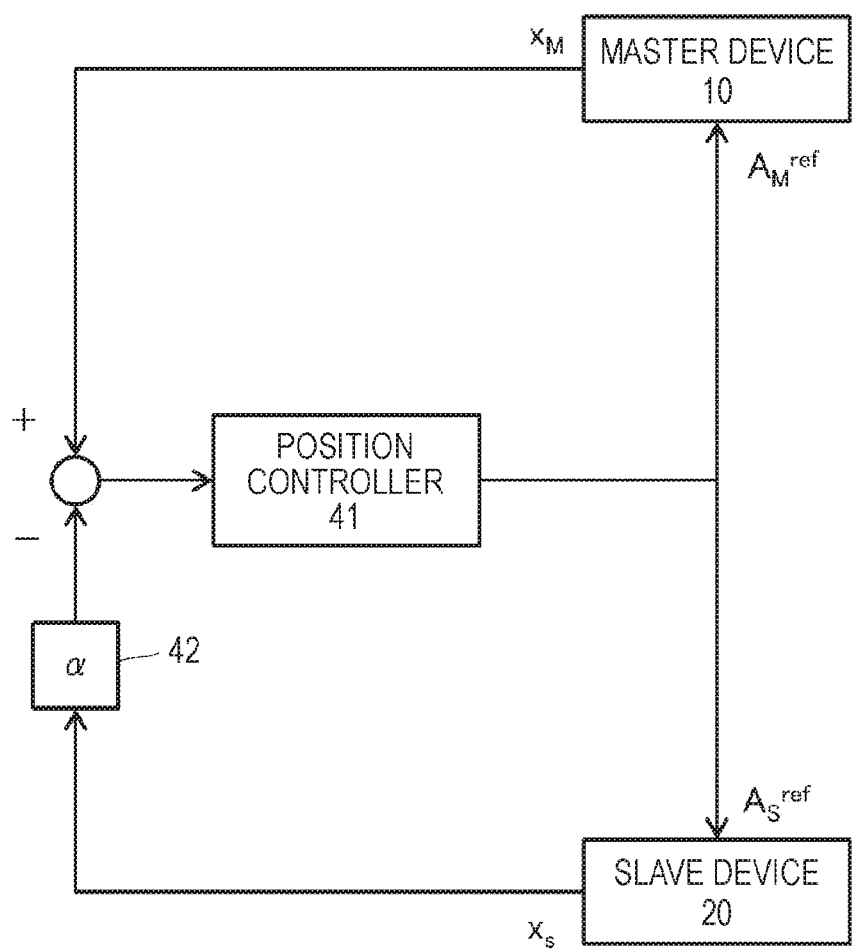
FIG. 4 is a diagram of an exemplary functional configuration of a position-symmetric bilateral control system 30.

In FIG. 4, an exemplary functional configuration of a position-symmetric bilateral control system 40 for performing bilateral control on the master device 10 and the slave device 20 is illustrated.

A position controller 41 supplies acceleration reference signals $A_M^{ref}$ and $A_S^{ref}$ respectively to the master device 10 and the slave device 20. The master device 10 performs acceleration control on the given acceleration reference signal $A_M^{ref}$, and a position and the posture $X_M$ of the robot (refer to FIG. 2) is displaced (however, X is vector representing six-dimensional position and posture, and A is second derivative of X (same applies below)). Similarly, the slave device 20 performs the acceleration control on the given acceleration reference signal $A_S^{ref}$, and a position and the posture $X_M$ of the robot (support arm device 300) is displaced.

Then, on the basis of a positional deviation between the master device 10 and the slave device 20, the position controller 41 supplies the acceleration reference signals $A_S^{ref}$ and $A_S^{ref}$ for driving the devices to a direction to correct this respectively to the master device 10 and the slave device 20. However, when the positional deviation between the master device 10 and the slave device 20 is calculated, a scaler 42 multiplies a position and posture signal $X_S$ of the slave device 20 by a coefficient α for position and posture space scaling between the master device 10 and the slave device 20.

Figure 5:
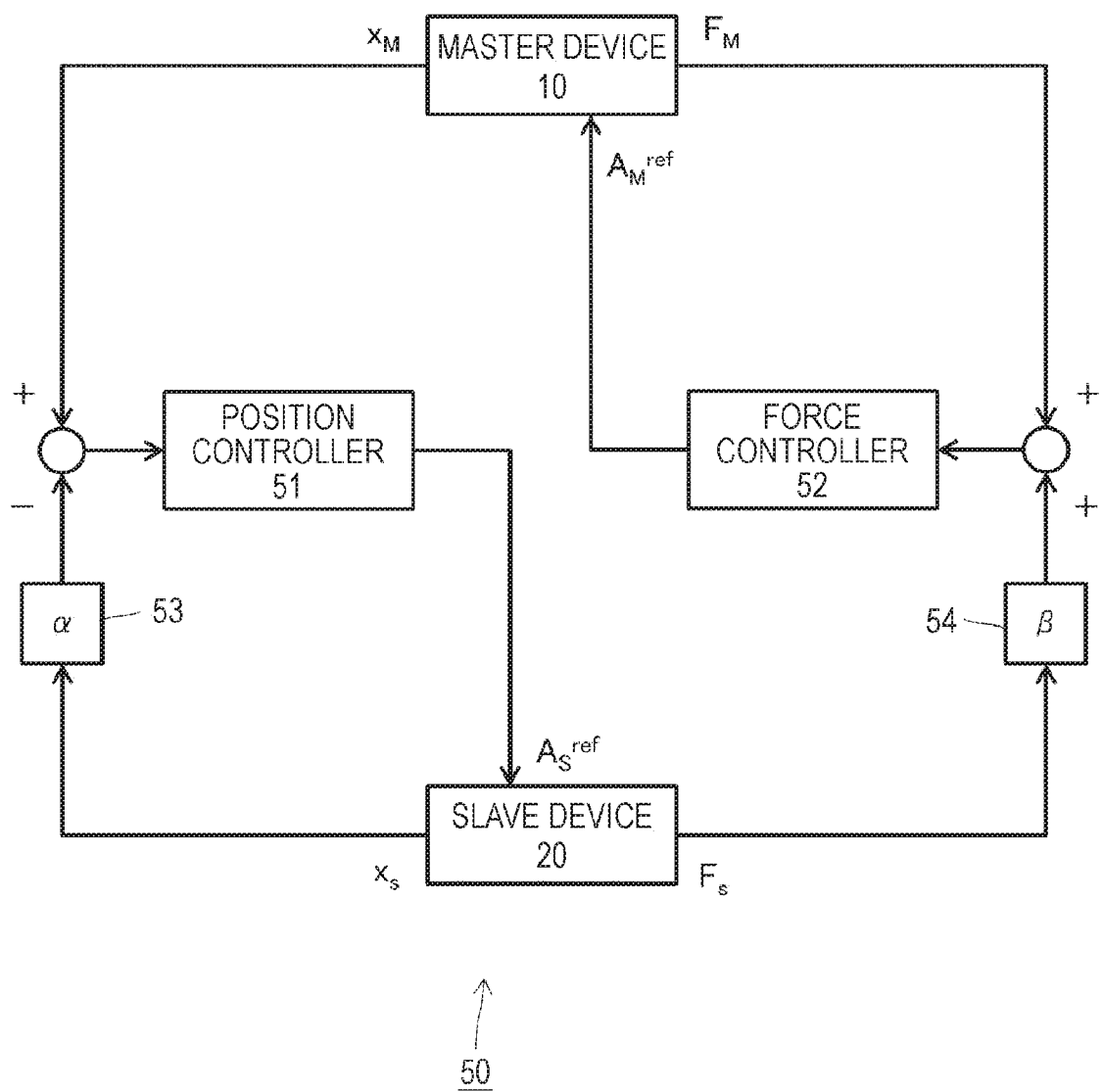
FIG. 5 is a diagram of an exemplary functional configuration of a force-feedback bilateral control system 40.

In FIG. 5, an exemplary functional configuration of a force-feedback bilateral control system 50 for performing bilateral control on the master device 10 and the slave device 20 is illustrated.

A position controller 51 supplies the acceleration reference signal $A_S^{ref}$ to the slave device 20. The slave device 20 performs the acceleration control on the given acceleration reference signal $A_S^{ref}$, and the position and the posture $X_S$ of the robot is displaced. Furthermore, in the slave device 20, an external force $F_S$ is generated according to a contact with a subject.

Furthermore, a force controller 52 supplies the acceleration reference signal $A_M^{ref}$ to the master device 10. The master device 10 performs the acceleration control on the given acceleration reference signal $A_M^{ref}$, and the position and the posture $X_M$ of the robot is displaced. Furthermore, in the master device 10, an external force $F_M$ is generated according to an operation by an operator.

On the basis of the positional deviation between the master device 10 and the slave device 20, the position controller 51 supplies the acceleration reference signal $A_S^{ref}$ for driving the devices to a direction to correct this to the slave device 20. However, when the positional deviation between the master device 10 and the slave device 20 is calculated, a scaler 53 multiplies the position and posture signal $X_S$ of the slave device 20 by the coefficient α for the position and posture space scaling between the master device 10 and the slave device 20.

Furthermore, the force controller 52 supplies the acceleration reference signal $A_S^{ref}$ to drive the devices to the direction to correct this to the master device 10 from a resultant force of the generated force of the master device 10 and the generated force of the slave device 20. However, when the resultant force of the generated forces of the master device 10 and the slave device 20 is calculated, a scaler 54 multiplies a force signal $F_S$ of the slave device 20 by a coefficient β for force space scaling between the master device 10 and the slave device 20.

Figure 6:
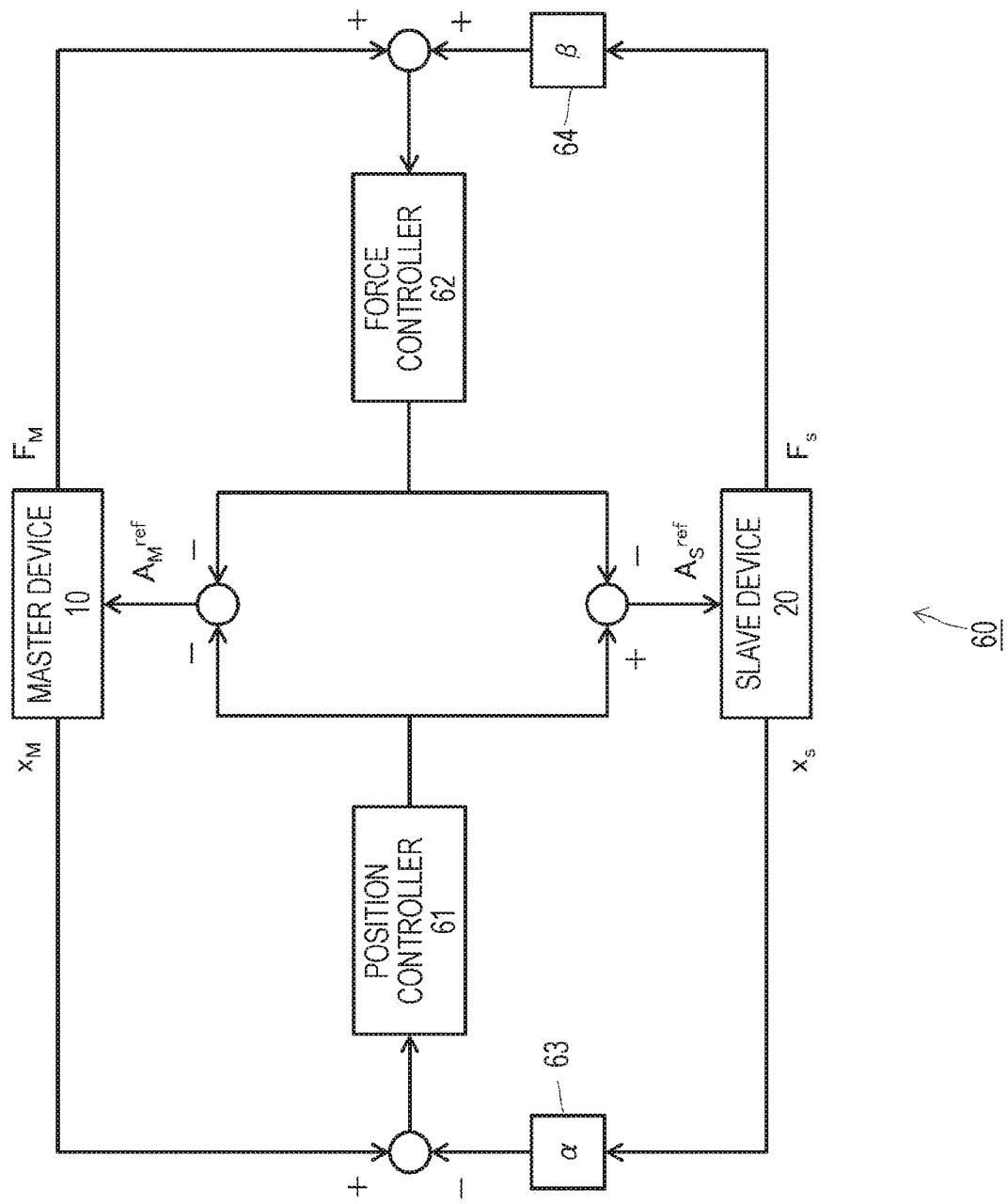
FIG. 6 is a diagram of an exemplary functional configuration of a 4CH type bilateral control system 50.

In FIG. 6, an exemplary functional configuration of a 4CH type bilateral control system 60 for performing bilateral control on the master device 10 and the slave device 20 is illustrated.

A position controller 61 outputs an acceleration reference signal to each of the master device 10 and the slave device 20. Furthermore, a force controller 62 outputs an acceleration reference signal to each of the master device 10 and the slave device 20. Then, a signal $A_M^{ref}$ obtained by adding both of the acceleration reference signals respectively supplied from the position controller 61 and the force controller 62 is supplied to the master device 10. Furthermore, a signal $A_S^{ref}$ obtained by adding both of the acceleration reference signals respectively supplied from the position controller 61 and the force controller 62 is supplied to the slave device 20.

The master device 10 performs the acceleration control on the acceleration reference signal $A_M^{ref}$, and the position and the posture $X_M$ of the robot is displaced. Furthermore, in the master device 10, an external force $F_M$ is generated according to an operation by an operator. Similarly, the slave device 20 performs the acceleration control on the acceleration reference signal $A_S^{ref}$, and the position and the posture $X_S$ of the robot is displaced. Furthermore, in the slave device 20, an external force $F_S$ is generated according to a contact with a subject.

On the basis of the positional deviation between the master device 10 and the slave device 20, the position controller 61 outputs the acceleration reference signal to each of the master device 10 and the slave device 20 for driving the devices to a direction to correct this. However, when the positional deviation between the master device 10 and the slave device 20 is calculated, a scaler 62 multiplies a position and posture signal $X_S$ of the slave device 20 by the coefficient α for the position and posture space scaling between the master device 10 and the slave device 20.

Furthermore, on the basis of a resultant force of the generated force $F_M$ of the master device 10 and the generated force $F_S$ of the slave device 20, the force controller 62 outputs an acceleration reference signal to each of the master device 10 and the slave device 20 for driving the devices to a direction to correct this. However, when a force deviation of the master device 10 and the slave device 20 is calculated, a scaler 64 multiplies the force signal $F_S$ of the slave device 20 by the coefficient β, for force space scaling between the master device 10 and the slave device 20.

Then, as described above, the signal $A_M^{ref}$ obtained by adding both of the acceleration reference signals respectively supplied from the position controller 61 and the force controller 62 is supplied to the master device 10. Furthermore, a signal $A_S^{ref}$ obtained by adding both of the acceleration reference signals respectively supplied from the position controller 61 and the force controller 62 is supplied to the slave device 20.

Here, a technology that incorporates a mechanism that feeds back the restraint force into the master-slave robot system 1 as illustrated in FIG. 1 will be described in detail below. According to the technology, it is possible for the user of the master device 10 to operate an arbitrary translational motion and rotational motion and realize an operation with high accuracy for tasks that are not formulated.

Figure 7:
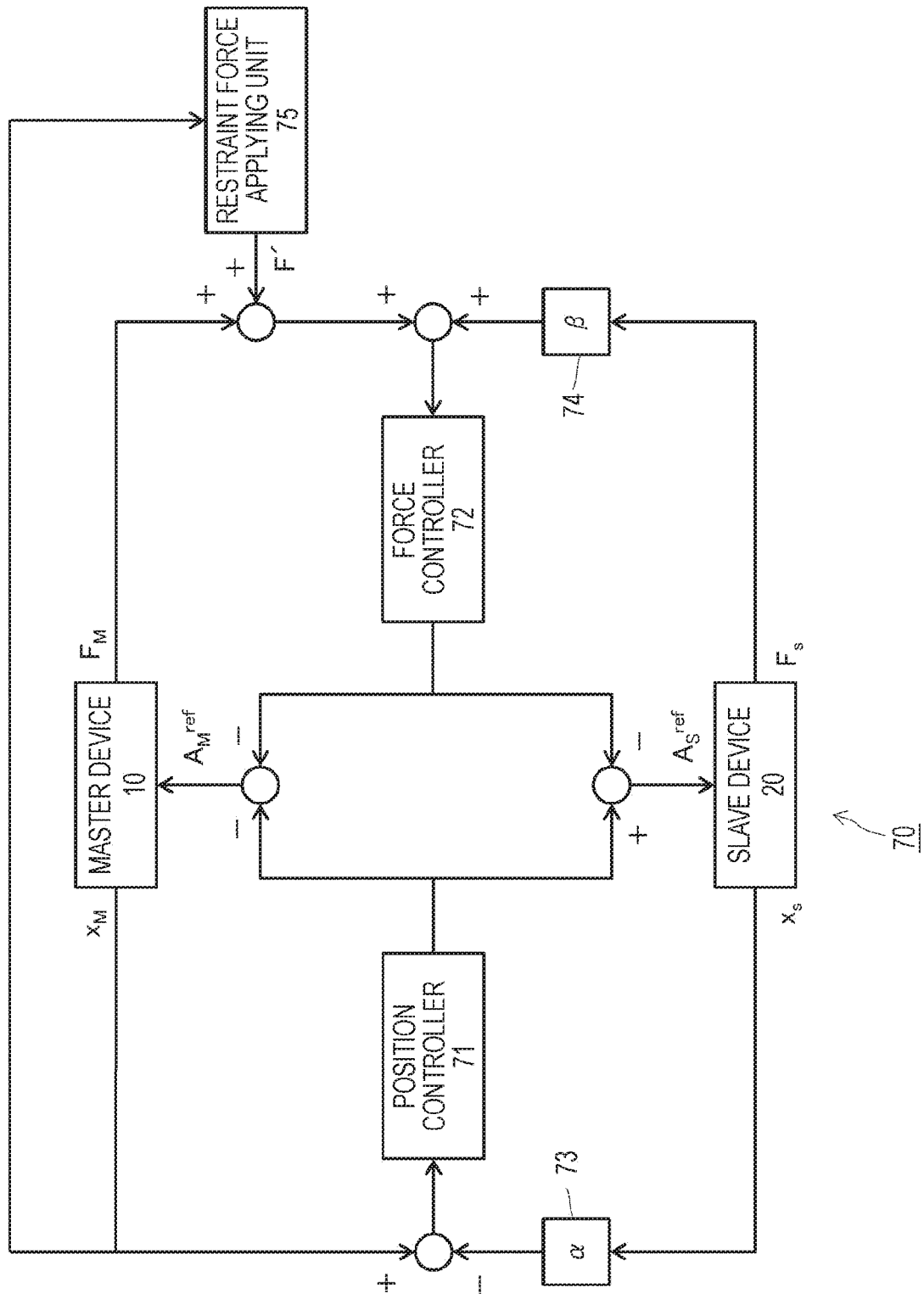
FIG. 7 is a diagram of an exemplary functional configuration of a 4CH bilateral control system 70 including a mechanism for applying a restraint force.

In FIG. 7, a functional configuration of a 4CH type bilateral control system 70 to which the technology disclosed herein is applied is schematically illustrated. The illustrated bilateral control system 70 has a main feature in that a mechanism that feeds back the restraint force is added to a bilateral control system of the master-slave robot.

A position controller 71 outputs an acceleration reference signal to each of the master device 10 and the slave device 20. Furthermore, a force controller 72 outputs an acceleration reference signal to each of the master device 10 and the slave device 20. Then, a signal $A_M^{ref}$ obtained by adding both of the acceleration reference signals respectively supplied from the position controller 71 and the force controller 72 is supplied to the master device 10. Furthermore, a signal $A_S^{ref}$ obtained by adding both of the acceleration reference signals respectively supplied from the position controller 71 and the force controller 72 is supplied to the slave device 20.

The master device 10 performs the acceleration control on the acceleration reference signal $A_M^{ref}$, and the position and the posture $X_M$ of the robot is displaced. Furthermore, in the master device 10, an external force $F_M$ is generated according to an operation by an operator. Similarly, the slave device 20 performs the acceleration control on the acceleration reference signal $A_S^{ref}$, and the position and the posture $X_S$ of the robot is displaced. Furthermore, in the slave device 20, an external force $F_S$ is generated according to a contact with a subject.

A scaler 73 multiplies the position and posture signal $X_S$ of the slave device 20 by the coefficient α for the position and posture space scaling between the master device 10 and the slave device 20. Furthermore, a scaler 74 multiplies the force signal $F_S$ of the slave device 20 by the coefficient β for the force space scaling between the master device 10 and the slave device 20.

A restraint force applying unit 75 generates a restraint force F' with reference to a current position or posture $X_M$ on the side of the master device 10. The restraint force F' is a virtual force that allows the master device 10 (or grip portion 220 thereof) to move only in a certain direction (for example, arbitrary translational or rotational direction). Details of processing for calculating the restraint force F' will be described later.

Note that the restraint force F' is not limited to acting on only in a uniaxial translational or rotational direction, and it is assumed that a plurality of translational or rotational directions may be employed.

On the basis of a resultant force of the generated force $F_M$ of the master device 10, the restraint force F', and a generated force $\beta F_S$ of the slave device 20, the force controller 72 outputs an acceleration reference signal to each of the master device 10 and the slave device 20 for driving the devices to a direction to correct this.

Furthermore, on the basis of a positional deviation ($X_M$−$\alpha X_S$) between the master device 10 and the slave device 20, the position controller 71 outputs the acceleration reference signal to each of the master device 10 and the slave device 20 for driving the devices to a direction to correct this.

Then, as described above, the signal $A_M^{ref}$ obtained by adding both of the acceleration reference signals respectively supplied from the position controller 71 and the force controller 72 is supplied to the master device 10. Furthermore, a signal $A_S^{ref}$ obtained by adding both of the acceleration reference signals respectively supplied from the position controller 71 and the force controller 72 is supplied to the slave device 20.

For example, there is a case where it is desired to translationally move the surgical instrument attached to the end effector of the slave device 20 in one axial direction or to allow the surgical instrument to perform the rotational motion during surgery. The restraint force applying unit 75 can apply a virtual restraint force to the master device 10 and the slave device 20 via the force controller 72, and the user can realize an operation including an arbitrary translational motion and rotational motion with high accuracy without causing a wobble.

The processing for generating the restraint force F' by the restraint force applying unit 75 can be realized by control by software at low cost. Furthermore, the user can directly instruct a timing when the restraint force F' is generated from the restraint force applying unit 75 via a UI such as the jog dial, the tact switch, the foot pedal, and the like. That is, the user is only required to instruct to generate the restraint force when the user desires to translationally or rotationally make the surgical instrument behave on the side of the slave device 20. For example, a button used to instruct to generate the restraint force may be mounted on the grip portion 220, and the generation of the restraint force may be instructed by a predetermined operation on the foot pedal switch. Of course, the generation timing of the restraint force may be automatically controlled by software control.

Figure 8:
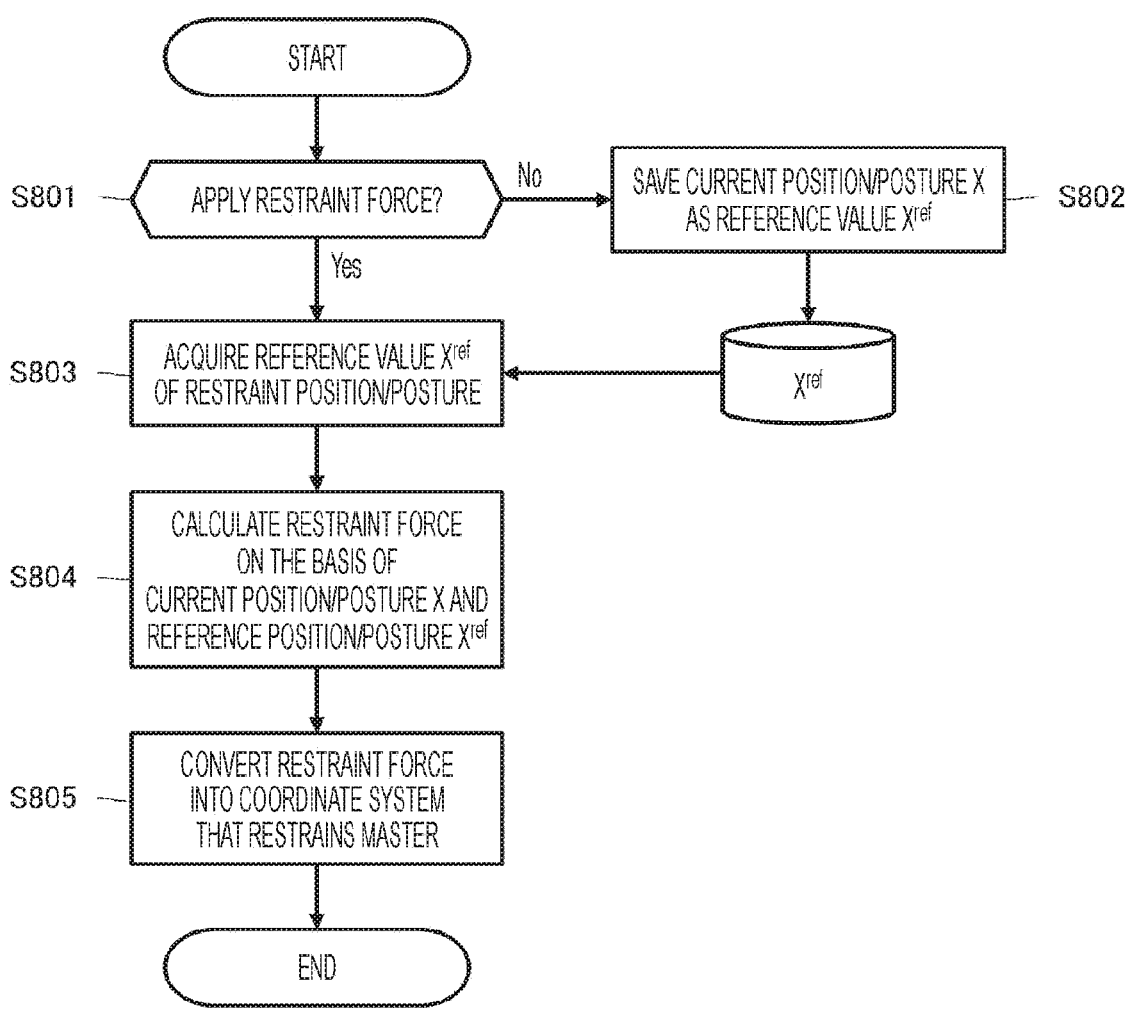
FIG. 8 is a flowchart of a processing procedure for applying a restraint force to the bilateral control system 70.

In FIG. 8, a processing procedure for applying a restraint force to the bilateral control system 70 is illustrated in a form of a flowchart. The illustrated processing procedure can be realized at low cost, for example, as software processing in the control system 30.

First, whether or not to apply the restraint force to the bilateral control system 70 is checked (step S801). For example, when the user instructs to apply the restraint force via the UI such as the jog dial, the tact switch, the foot pedal switch, and the like on the side of the master device 10, it is determined to apply the restraint force.

Here, when it is determined not to apply the restraint force (No in step S801), the current position and posture X of the side of the master device 10 (for example, grip portion 220) is temporarily saved as a reference value $X^{ref}$ of a position and posture to be restrained when the restraint force is applied later (step S802).

On the other hand, when it is determined to apply the restraint force (Yes in step S801), the restraint position/posture reference value $X^{ref}$ that has been saved in step S802 one control cycle before is acquired (step S803).

Then, the current position and posture X of the master device 10 is acquired, and a restraint force F according to a difference between the current position and posture X and the restraint position/posture reference value $X^{ref}$ is calculated according to the following equation (1) (step S804). However, in the equation (1), the reference C is a coefficient indicating a gain. Furthermore, the equation (1) derives the restraint force F only by a proportional gain. However, it goes without saying that the restraint force F can be derived by using other position control method.

[Math. 1]

$$F = C(X^{ref} - X) \quad (1)$$

Next, the calculated restraint force F is converted into a coordinate system that actually restrains the master device 10 according to the following equation (2) (step S805) and is output as a virtual restraint force F'. As a result, the restraint force F' that restrains the master device 10 to the restraint position/posture reference value $X^{ref}$ is applied to the master device 10.

[Math. 2]

$$F' = \mathrm{Trans}(F) \quad (2)$$

For example, in a case where it is desired to restrain the drive of the master-slave robot in a certain translational direction, positional information to be the reference (that is, restraint condition) is acquired as the reference value $X^{ref}$ in step S803. Then, in subsequent steps S804 and S805, the restraint forces F and F' are generated that increase as the position of the master device 10 is separated from the reference value $X^{ref}$.

Furthermore, in a case where it is desired to restrain the drive of the master-slave robot in a certain rotational direction, posture information to be the reference (that is, restraint condition) is acquired as the reference value $X^{ref}$ in step S803. Then, in subsequent steps S804 and S805, the restraint forces F and F' are generated that increase as the posture of the master device 10 is separated from the reference value $X^{ref}$.

When the user remotely operates the slave device 20 from the master device 10 by using the grip portion 220, the restraint force F' to drive the grip portion 220 in an arbitrary translational or rotational direction acts on the grip portion 220. Therefore, the user can improve accuracy in the remote operation of the slave device 20 while receiving a support or assistance of such a restraint force F', and a task processing time (treatment time and the like) can be shortened.

Furthermore, the restraint force can be applied while driving the robot system 1 including the master device 10 and the slave device 20 constantly in a bilateral control mode, that is, without switching a control mode. The user can safely perform an operation while feeling a contact force of the side of the slave device 20 (forceps 323) with a subject, regarding a behavior in an unrestrained direction.

Note that, in a case where the grip portion 220 includes the input means such as the jog dial, the tact switch, and the like, in step S801 described above, the user can instruct to apply the restraint force via this type of input means. Furthermore, in a case where the grip portions 220L and 220R are respectively prepared for the left and right hands as illustrated in FIG. 2, the restraint force may be applied only to the instructed grip portion 220L or 220R in a case where it is instructed to apply the restraint force to only one of the grip portion 220L or 220R. Alternatively, in step S801, it is possible to determine whether or not to separately apply the restraint force to the left grip portion 220L or the right grip portion 220R by automatic control.

In FIG. 7, an exemplary configuration of the system 70 in which the restraint force applying unit 75 is disposed at a place where the restraint force is fed back to the force controller 72 is illustrated. The place where the restraint force is fed back is not limited to this.

Figure 9:
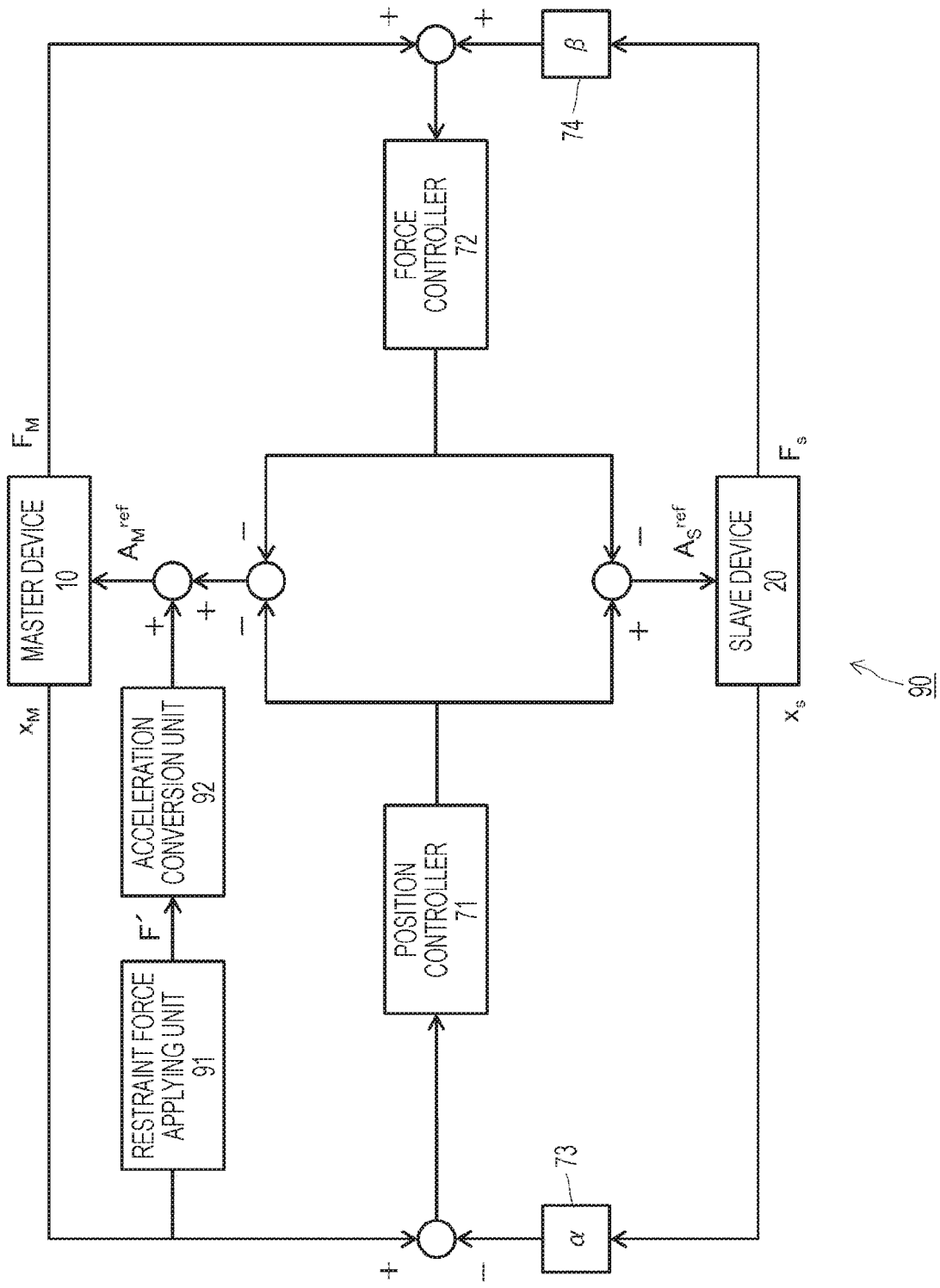
FIG. 9 is a diagram of an exemplary functional configuration of a 4CH bilateral control system 90 including a mechanism for applying a restraint force.

In FIG. 9, an exemplary configuration of a bilateral control system 90 that feeds back the restraint force to the master device 10 is illustrated. However, a component same as that in the system 70 illustrated in FIG. 7 is denoted with the same reference number.

A restraint force applying unit 91 calculates the restraint force F according to the difference between the current position and posture $X_M$ of the master device 10 and the restraint position/posture reference value $X^{ref}$ and further converts the restraint force F into the coordinate system that actually restrains the master device 10 so as to obtain the restraint force F'. The restraint force F' is a virtual force that allows the master device 10 (or grip portion 220 thereof) to move only in a certain direction (for example, arbitrary translational or rotational direction). However, for example, the restraint force F' can be calculated according to the processing procedure illustrated in FIG. 8. Next, an acceleration conversion unit 92 converts the calculated restraint force F' into an acceleration dimension signal.

Then, an acceleration signal $A_M^{ref}$ obtained by applying an acceleration component caused by the restraint force F' in addition to the acceleration reference signals respectively supplied from the position controller 71 and the force controller 72 is supplied to the master device 10.

For example, there is a case where it is desired to translationally move the surgical instrument attached to the end effector of the slave device 20 in one axial direction or to allow the surgical instrument to perform the rotational motion during surgery. The restraint force applying unit 91 can apply a virtual restraint force to the master device 10 and the slave device 20, and the user can realize an operation including an arbitrary translational motion and rotational motion with high accuracy without causing a wobble.

In FIGS. 7 and 9, the exemplary system configurations are illustrated in which the restraint force that causes the master device 10 and the slave device 20 to move only in a certain direction is applied. As an application example of the above system configuration, a system can be configured to apply a restraint force for restraining all the six degrees of freedom of position and posture.

For example, a case is assumed where a user who is an operator desires (or need) to release his/her hand from the grip portion 220 and to temporarily perform a work other than the remote operation of the slave device 20 during surgery. In a case where force control is applied to the robot system 1, there is a possibility that a deflection caused by a weight of the grip portion 220 is erroneously input. Furthermore, even if weight compensation is applied to the force control, there is a possibility that the side of the slave device 20 behaves by a noise component of the force sensor.

Therefore, it is considered that the function for applying the restraint force to restrain all the six degrees of freedom of the position and the posture is useful in a case where it is desired to keep the master-slave robot at the current position and posture under a certain condition.

Figure 10:
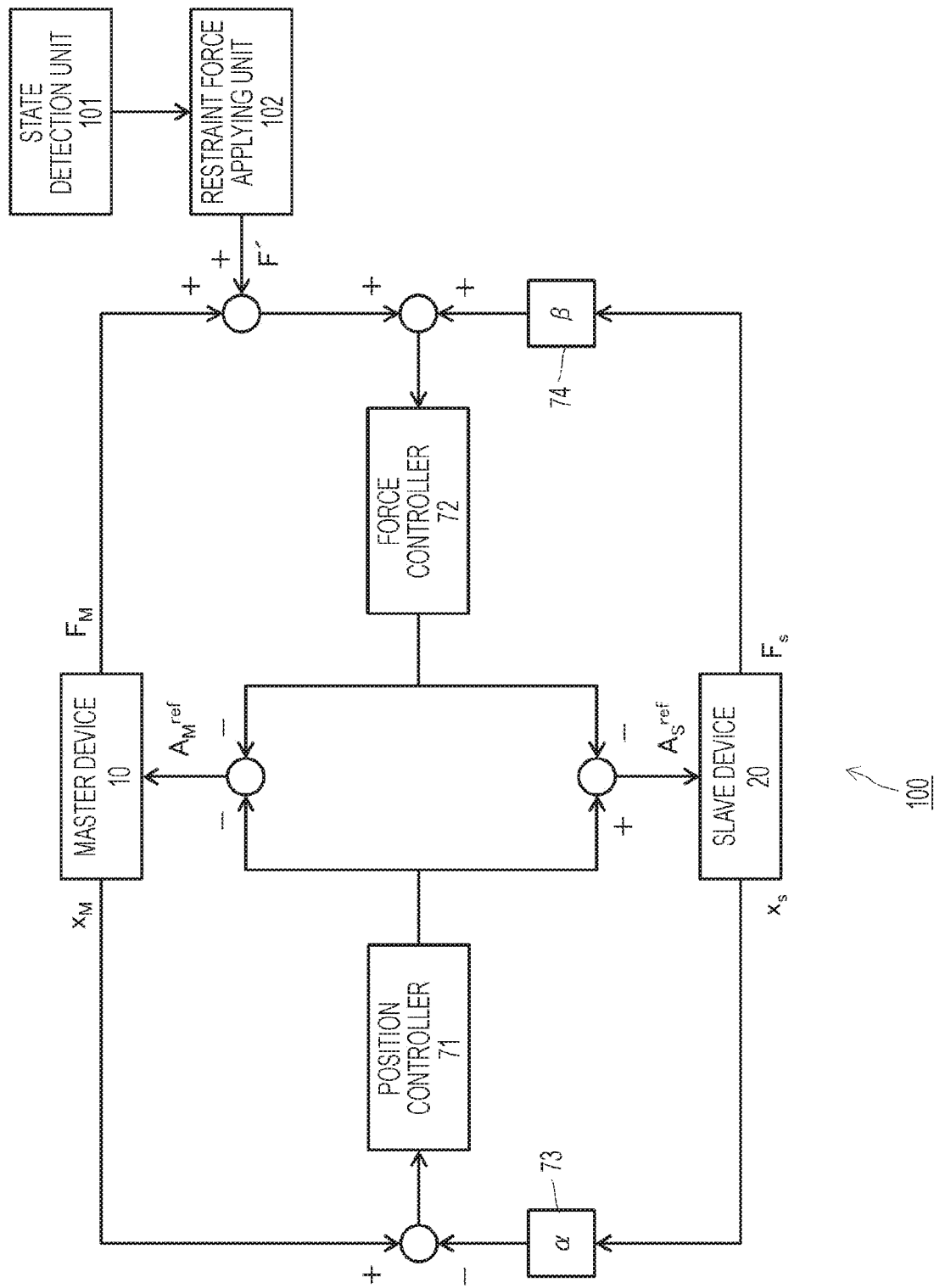
FIG. 10 is a diagram of an exemplary configuration of a bilateral control system 100 that feeds back the restraint force for keeping a master-slave robot at a current position and posture.

In FIG. 10, an exemplary configuration of a bilateral control system 1000 that feeds back the restraint force for keeping the master-slave robot at the current position and posture is illustrated. However, a component same as that in the system 70 illustrated in FIG. 7 is denoted with the same reference number.

A state detection unit 101 detects a state of the grip portion 220 on the side of the master device 10, that is, whether or not the state is a holding state. The state detection unit 101 includes, for example, the force sensor that detects the external force added to the grip portion 220, the pressure sensor, the human sensor, or the like that senses a fingertip of the user (as described above).

Then, a restraint force applying unit 102 outputs a restraint force in a case where the state detection unit 101 determines that the grip portion 220 is not in the holding state. Alternatively, the restraint force applying unit 102 may output the restraint force in response to an instruction to apply the restraint force via the input means such as the jog dial, the tact switch, and the like provided on the grip portion 220.

The restraint force applying unit 102 calculates the restraint force F according to the difference between the current position and posture $X_M$ of the master device 10 and the restraint position/posture reference value $X^{ref}$ and further converts the restraint force F into the coordinate system that actually restrains the master device 10 so as to obtain the restraint force F'. In the exemplary system configurations illustrated in FIGS. 7 and 9, the restraint force for restraining the drive of the master-slave robot to an arbitrary translational or rotational direction is applied (as described above). On the other hand, in the example illustrated in FIG. 10, the restraint force for keeping the master-slave robot at the current position and posture is applied. Details of processing for calculating such a restraint force will be described later.

On the basis of a resultant force of the generated force $F_M$ of the master device 10, the restraint force F', and a generated force $\beta F_S$ of the slave device 20, the force controller 72 outputs an acceleration reference signal to each of the master device 10 and the slave device 20 for driving the devices to a direction to correct this.

Furthermore, on the basis of a positional deviation ($X_M$-$\alpha X_S$) between the master device 10 and the slave device 20, the position controller 71 outputs the acceleration reference signal to each of the master device 10 and the slave device 20 for driving the devices to a direction to correct this.

Then, the signal $A_M^{ref}$ obtained by adding both the acceleration reference signals respectively supplied from the position controller 61 and the force controller 62 is supplied to the master device 10, and the signal $A_S^{ref}$ obtained by adding both the acceleration reference signals respectively supplied from the position controller 61 and the force controller 62 is supplied to the slave device 20.

For example, in a case where the user who is the operator releases his/her hand from the grip portion 220 during surgery, the restraint force for restraining all the six degrees of freedom of the master-slave robot is applied, and the master-slave robot can be kept at the current position and posture. It is possible for the user to release his/her hand from the grip portion 220 and temporarily perform a work other than the remote operation of the slave device 20.

Note that the system 100 illustrated in FIG. 10 has a configuration in which the restraint force for keeping the master-slave robot at the current position and posture is fed back to the force controller 72. However, the place where the restraint force is fed back is not limited to this. For example, as illustrated in FIG. 9, it is possible to convert the restraint force for restraining all the six degrees of freedom into the acceleration dimension and to feed back such a restraint force to the master device 10.

Figure 11:
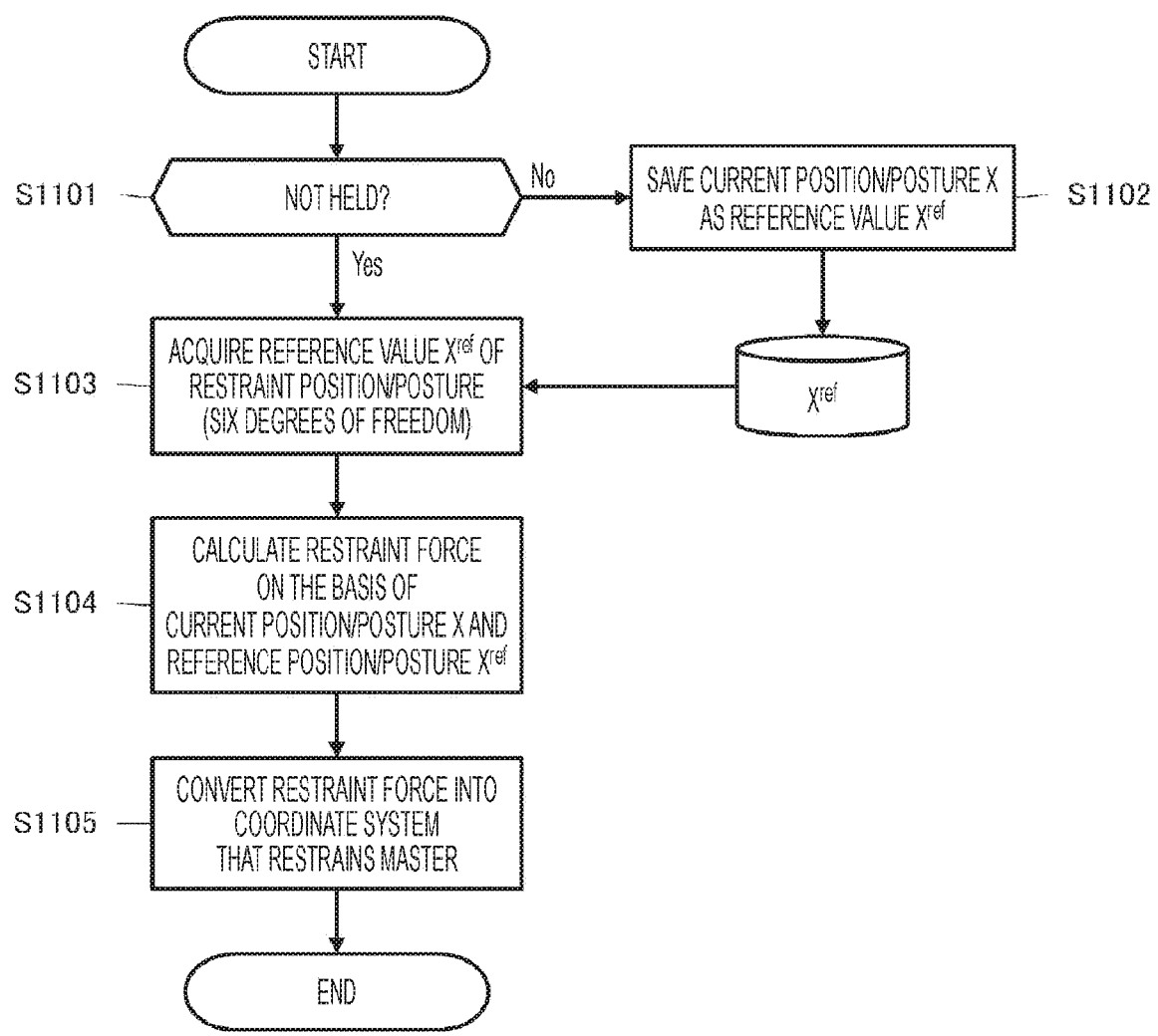
FIG. 11 is a flowchart of a processing procedure for applying the restraint force to the bilateral control system 100 to keep the bilateral control system 100 at the current position and posture.

In FIG. 11, a processing procedure for applying the restraint force to keep the bilateral control system 100 at the current position and posture is illustrated in a form of a flowchart. The illustrated processing procedure can be realized at low cost, for example, as software processing in the control system 30.

First, whether or not the grip portion 220 on the side of the master device 10 is in the holding state in which the grip portion 220 is gripped or held by the user is checked (step S1101). It is assumed that the state detection unit 101 that detects whether or not the grip portion 220 is in the holding state is provided on the grip portion 220 (as described above).

Here, when it is determined that the grip portion 220 is in the holding state by the user (No in step S1101), the restraint force for keeping the grip portion 220 at the current position and posture is unnecessary. In this case, the current position and posture X of the side of the master device 10 (for example, grip portion 220) is temporarily saved as a reference value $X^{ref}$ of a position and posture to be restrained when the restraint force is applied later (step S1102).

On the other hand, when it is determined that the grip portion 220 is not in the holding state by the user, in other words, in a state out of the operation by the user (Yes in step S1101), the restraint force for keeping the grip portion 220 at the current position and posture is needed. In this case, the restraint position/posture reference value $X^{ref}$ having six degrees of freedom in total that has been saved one control cycle before in step S1102 is acquired (step S1103).

Then, the current position and posture X of the master device 10 is acquired, and a restraint force F according to a difference between the current position and posture X and the restraint position/posture reference value $X^{ref}$ is calculated according to the above equation (1) (step S1104). Next, the calculated restraint force F is converted into a coordinate system that actually restrains the master device 10 according to the above equation (2) (step S1105) and is output as a virtual restraint force F'. As a result, to the master device 10, the position and posture reference value $X^{ref}$ that restrains six degrees of freedom, that is, the restraint force F' for keeping the master device 10 at the current position and posture is applied.

When the user remotely operates the slave device 20 from the master device 10 by using the grip portion 220, the restraint force F' to drive the grip portion 220 in an arbitrary translational or rotational direction acts on the grip portion 220. Therefore, the user can improve accuracy in the remote operation of the slave device 20 while receiving a support or assistance of such a restraint force F', and a task processing time (treatment time and the like) can be shortened.

So far, the system configuration in which the restraint force is applied to the 4CH type bilateral control system has been described. However, by providing a mechanism for applying the restraint force in a bilateral control system other than the 4CH type, a similar effect can be obtained.

Figure 12:
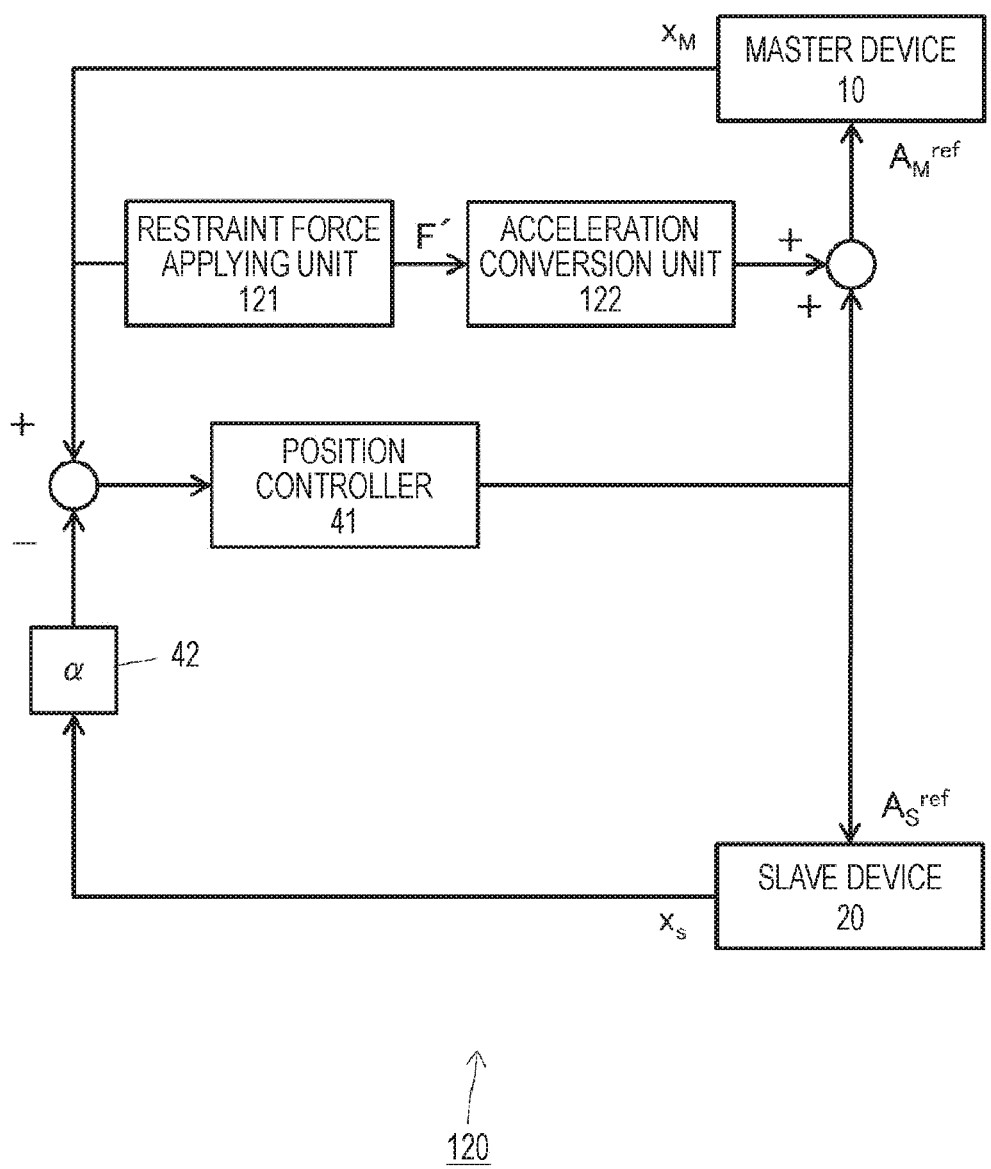
FIG. 12 is a diagram of a functional configuration of a position-symmetric bilateral control system 140 to which the technology disclosed herein is applied.

In FIG. 12, a functional configuration of a position-symmetric bilateral control system 120 to which the technology disclosed herein is applied is schematically illustrated. However, a component same as that in the system 40 illustrated in FIG. 4 is denoted with the same reference number.

A position controller 41 supplies acceleration reference signals $A_M^{ref}$ and $A_S^{ref}$ respectively to the master device 10 and the slave device 20. The master device 10 performs the acceleration control on the acceleration reference signal $A_M^{ref}$, and the position and the posture $X_M$ of the robot is displaced. Similarly, the slave device 20 performs the acceleration control on the acceleration reference signal $A_S^{ref}$, and the position and the posture $X_S$ of the robot is displaced.

On the basis of a positional deviation between the master device 10 and the slave device 20, the position controller 41 supplies the acceleration reference signals $A_M^{ref}$ and $A_S^{ref}$ for driving the devices to a direction to correct this respectively to the master device 10 and the slave device 20. However, when the positional deviation between the master device 10 and the slave device 20 is calculated, a scaler 42 multiplies a position and posture signal $X_S$ of the slave device 20 by a coefficient α for position and posture space scaling between the master device 10 and the slave device 20.

Furthermore, a restraint force applying unit 121 calculates the restraint force F according to the difference between the current position and posture $X_M$ of the master device 10 and the restraint position/posture reference value $X^{ref}$ and further converts the restraint force F into the coordinate system that actually restrains the master device 10 so as to obtain the restraint force F'. Moreover, an acceleration conversion unit 122 converts the calculated restraint force F' into an acceleration dimension signal.

Then, an acceleration signal $A_M^{ref}$ obtained by applying an acceleration component caused by the restraint force F' in addition to the acceleration reference signal supplied from the position controller 41 is supplied to the master device 10.

Note that the restraint force F' output by the restraint force applying unit 121 is a virtual force that allows the master device 10 (or grip portion 220 thereof) to move only in a certain direction (for example, arbitrary translational or rotational direction). However, for example, the restraint force F' can be calculated according to the processing procedure illustrated in FIG. 8. However, the restraint force applying unit 121 may output the restraint force for keeping the grip portion 220 at the current position and posture (that is, restraining all the six degrees of freedom) in a state where the grip portion 220 is not held. In the latter case, for example, the restraint force can be calculated according to the processing procedure illustrated in FIG. 11.

Figure 13:
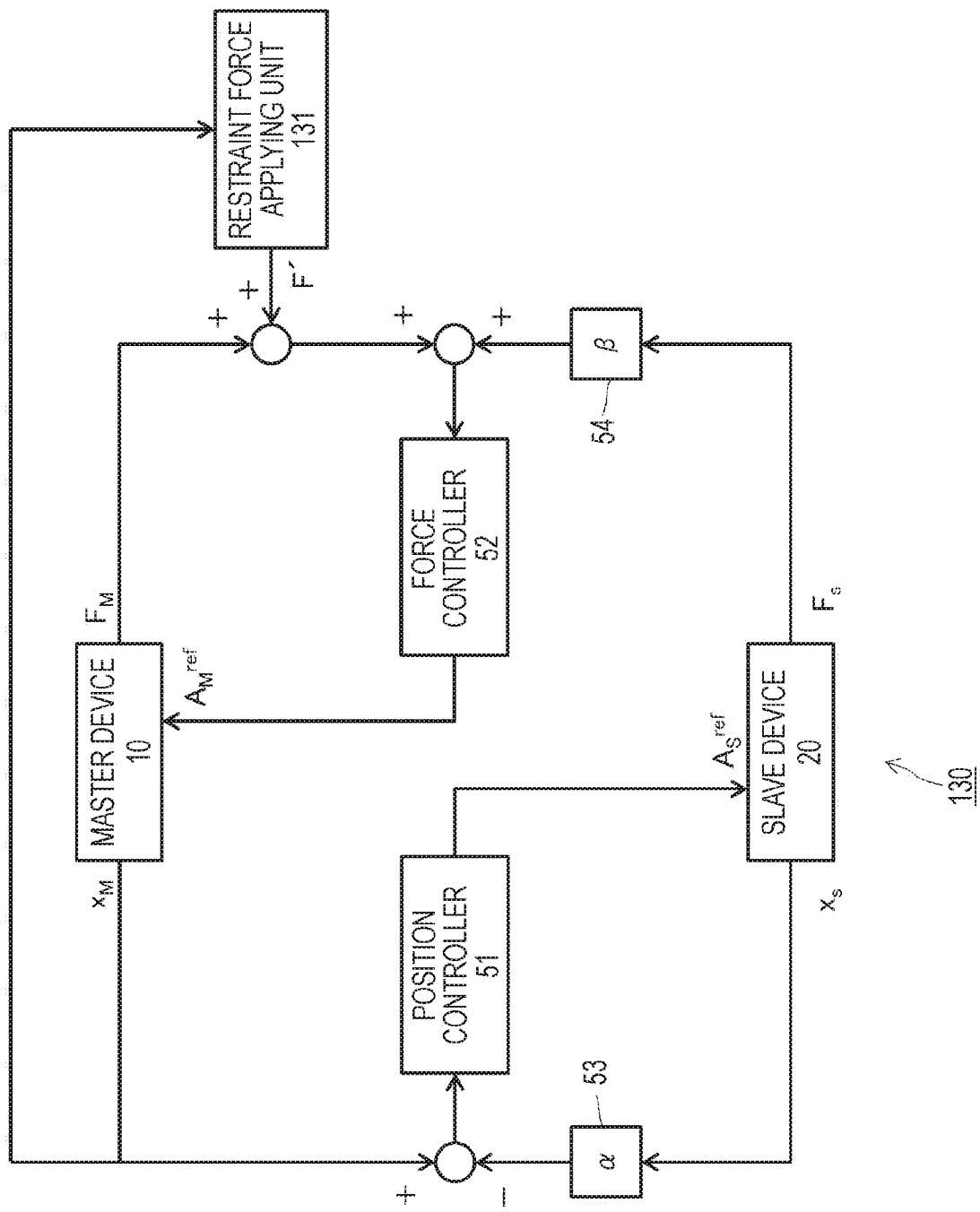
FIG. 13 is a diagram of a functional configuration of a force-feedback bilateral control system 140 to which the technology disclosed herein is applied.

In FIG. 13, a functional configuration of a force-feedback bilateral control system 130 to which the technology disclosed herein is applied is schematically illustrated. However, a component same as that in the system 50 illustrated in FIG. 5 is denoted with the same reference number.

A position controller 51 supplies the acceleration reference signal $A_S^{ref}$ to the slave device 20. The slave device 20 performs the acceleration control on the acceleration reference signal $A_S^{ref}$, and the position and the posture $X_S$ of the robot is displaced. Furthermore, in the slave device 20, an external force $F_S$ is generated according to a contact with a subject.

Furthermore, a force controller 52 supplies the acceleration reference signal $A_M^{ref}$ to the master device 10. The master device 10 performs the acceleration control on the acceleration reference signal $A_M^{ref}$, and the position and the posture $X_M$ of the robot is displaced. Furthermore, in the master device 10, an external force $F_M$ is generated according to an operation by an operator.

On the basis of the positional deviation between the master device 10 and the slave device 20, the position controller 51 supplies the acceleration reference signal $A_S^{ref}$ for driving the devices to a direction to correct this to the slave device 20. However, when the positional deviation between the master device 10 and the slave device 20 is calculated, a scaler 53 multiplies the position and posture signal $X_S$ of the slave device 20 by the coefficient α for the position and posture space scaling between the master device 10 and the slave device 20.

A restraint force generation unit 131 calculates the restraint force F according to the difference between the current position and posture $X_M$ of the master device 10 and the restraint position/posture reference value $X^{ref}$ and further converts the restraint force F into the coordinate system that actually restrains the master device 10 so as to obtain the restraint force F'.

Then, the force controller 52 supplies the acceleration reference signal $A_S^{ref}$ to drive the devices to the direction to correct this from a resultant force of the generated force of the master device 10, the generated force of the slave device 20, and the restraint force F' to the master device 10. However, a scaler 54 multiplies the force signal $F_S$ of the slave device 20 by the coefficient β for the force space scaling between the master device 10 and the slave device 20.

Note that the restraint force F' output by the restraint force applying unit 131 is a virtual force that allows the master device 10 (or grip portion 220 thereof) to move only in a certain direction (for example, arbitrary translational or rotational direction). However, for example, the restraint force F' can be calculated according to the processing procedure illustrated in FIG. 8. However, the restraint force applying unit 131 may output the restraint force for keeping the grip portion 220 at the current position and posture (that is, restraining all the six degrees of freedom) in a state where the grip portion 220 is not held. In the latter case, for example, the restraint force can be calculated according to the processing procedure illustrated in FIG. 11.

Figure 14:
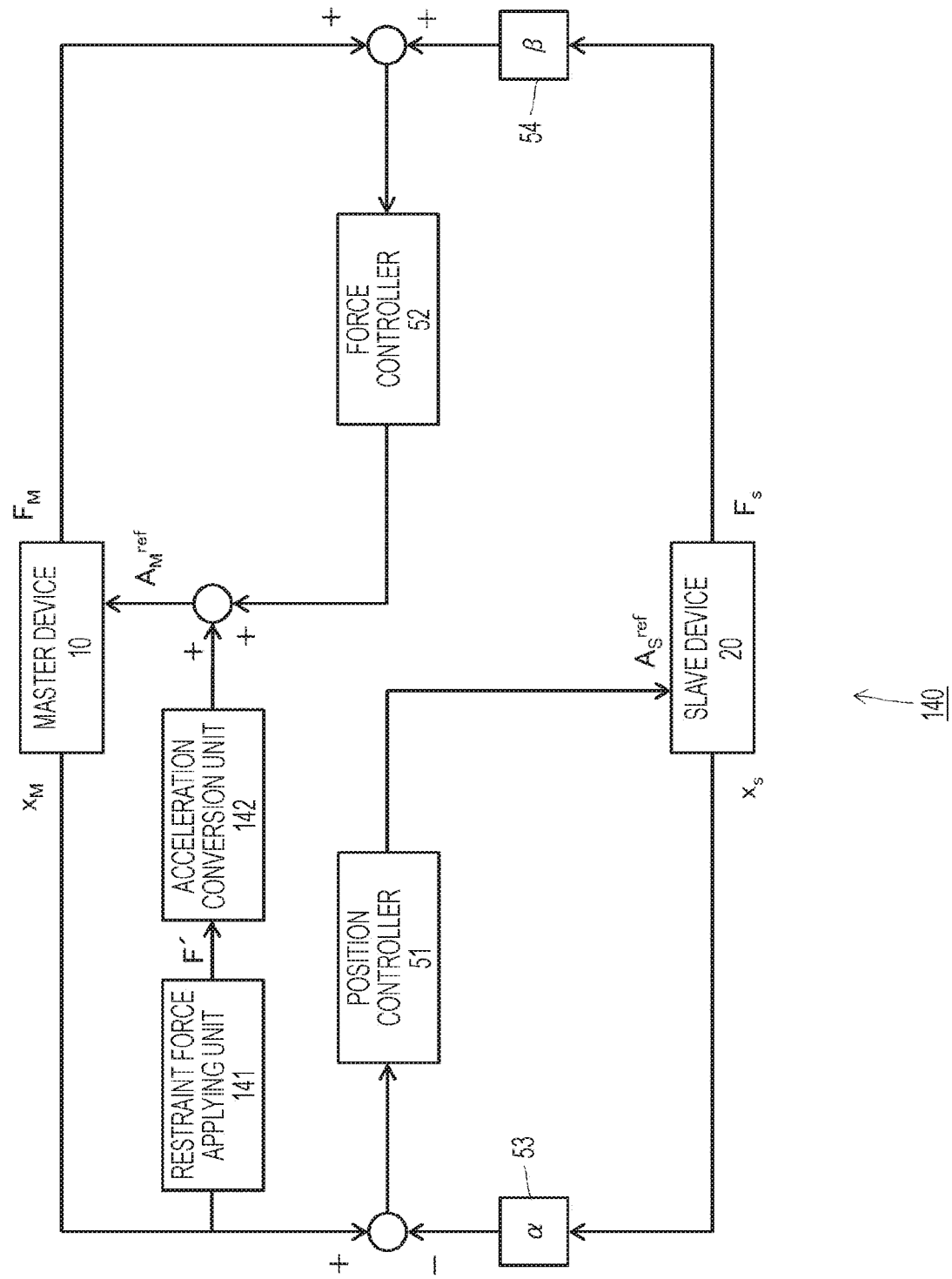
FIG. 14 is a diagram of a functional configuration of the force-feedback bilateral control system 140 to which the technology disclosed herein is applied.

Furthermore, in FIG. 14, another functional configuration of a force-feedback bilateral control system 140 to which the technology disclosed herein is applied is schematically illustrated. However, a component same as that in the system 50 illustrated in FIG. 13 is denoted with the same reference number. The illustrated system 140 has a configuration in which the restraint force is converted into the acceleration dimension and is applied to the bilateral control system, and the place where the restraint force is fed back is different from that of the system 130 illustrated in FIG. 13.

A restraint force applying unit 141 calculates the restraint force F according to the difference between the current position and posture $X_M$ of the master device 10 and the restraint position/posture reference value $X^{ref}$ and further converts the restraint force F into the coordinate system that actually restrains the master device 10 so as to obtain the restraint force F'. Next, an acceleration conversion unit 142 converts the calculated restraint force F' into an acceleration dimension signal.

Then, an acceleration signal $A_M^{ref}$ obtained by applying an acceleration component caused by the restraint force F' in addition to the acceleration reference signal supplied from the force controller 52 is supplied to the master device 10.

Note that the restraint force F' output by the restraint force applying unit 141 is a virtual force that allows the master device 10 (or grip portion 220 thereof) to move only in a certain direction (for example, arbitrary translational or rotational direction). However, for example, the restraint force F' can be calculated according to the processing procedure illustrated in FIG. 8. However, the restraint force applying unit 141 may output the restraint force for keeping the grip portion 220 at the current position and posture (that is, restraining all the six degrees of freedom) in a state where the grip portion 220 is not held. In the latter case, for example, the restraint force can be calculated according to the processing procedure illustrated in FIG. 11.

Furthermore, so far, the system configuration in which the restraint force is applied to the bilateral control system has been described. However, by providing a mechanism for applying the restraint force in a unilateral control system, a similar effect can be obtained.

Figure 15:
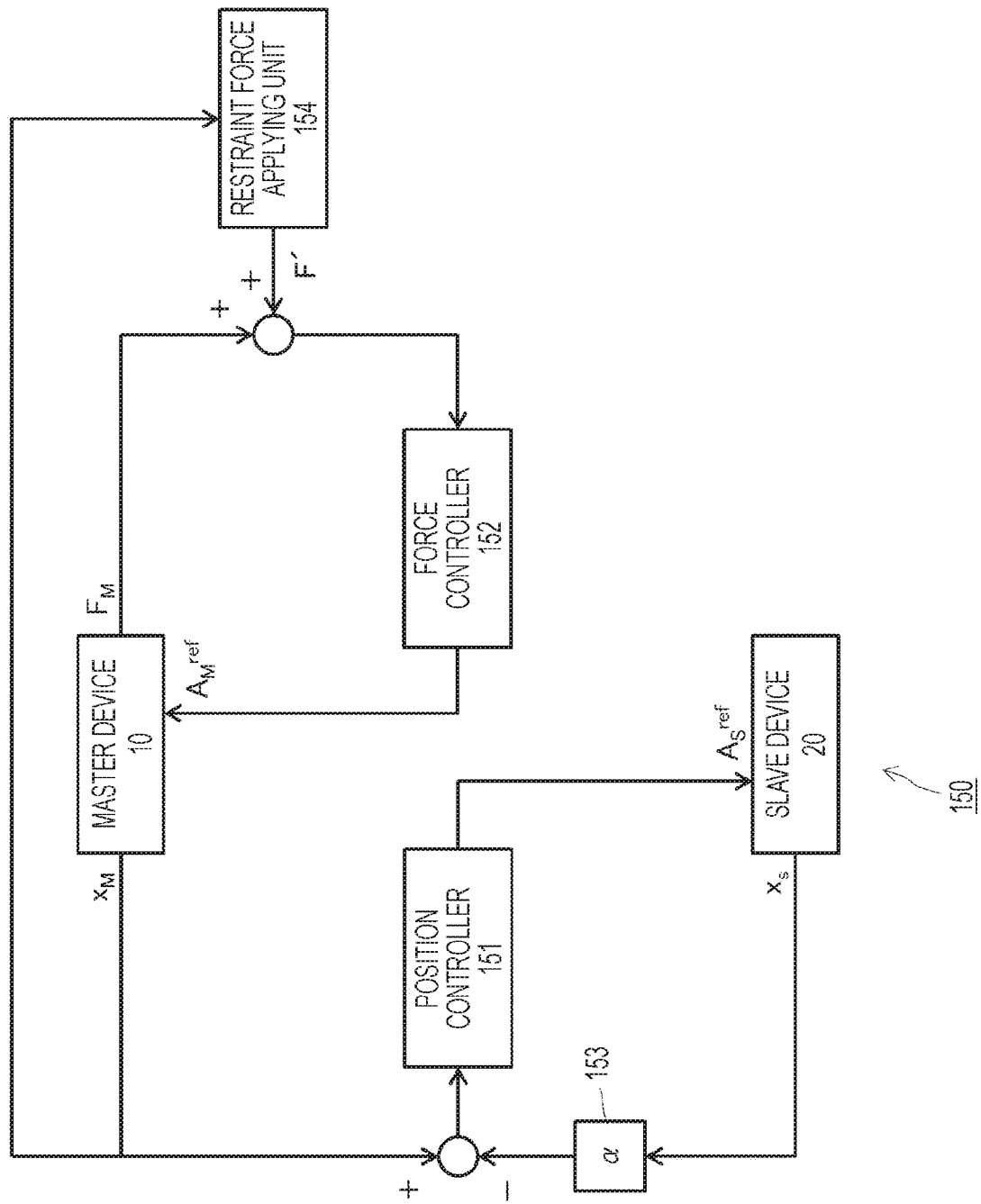
FIG. 15 is a diagram of a functional configuration of a unilateral control system 150 to which the technology disclosed herein is applied.

In FIG. 15, a functional configuration of a unilateral control system 150 to which the technology disclosed herein is applied is schematically illustrated.

A position controller 151 supplies an acceleration reference signal $A_S^{ref}$ to the slave device 20. The slave device 20 performs the acceleration control on the acceleration reference signal $A_S^{ref}$, and the position and the posture $X_S$ of the robot is displaced. Furthermore, in the slave device 20, an external force $F_S$ is generated according to a contact with a subject.

Furthermore, a force controller 152 supplies an acceleration reference signal $A_M^{ref}$ to the master device 10. The master device 10 performs the acceleration control on the acceleration reference signal $A_M^{ref}$, and the position and the posture $X_M$ of the robot is displaced. Furthermore, in the master device 10, an external force $F_M$ is generated according to an operation by an operator.

On the basis of the positional deviation between the master device 10 and the slave device 20, the position controller 151 supplies the acceleration reference signal $A_S^{ref}$ for driving the devices to a direction to correct this to the slave device 20. However, when the positional deviation between the master device 10 and the slave device 20 is calculated, a scaler 153 multiplies the position and posture signal $X_S$ of the slave device 20 by the coefficient α for the position and posture space scaling between the master device 10 and the slave device 20.

A restraint force applying unit 154 calculates the restraint force F according to the difference between the current position and posture $X_M$ of the master device 10 and the restraint position/posture reference value $X^{ref}$ and further converts the restraint force F into the coordinate system that actually restrains the master device 10 so as to obtain the restraint force F'.

Then, the force controller 152 supplies the acceleration reference signal $A_S^{ref}$ to drive the devices to the direction to correct this from a resultant force of the generated force $F_M$ of the master device 10 and the restraint force F' output from the restraint force applying unit 154 to the master device 10.

Note that the restraint force F' output by the restraint force applying unit 154 is a virtual force that allows the master device 10 (or grip portion 220 thereof) to move only in a certain direction (for example, arbitrary translational or rotational direction). However, for example, the restraint force F' can be calculated according to the processing procedure illustrated in FIG. 8. However, the restraint force applying unit 154 may output the restraint force for keeping the grip portion 220 at the current position and posture (that is, restraining all the six degrees of freedom) in a state where the grip portion 220 is not held. In the latter case, for example, the restraint force can be calculated according to the processing procedure illustrated in FIG. 11.

Figure 16:
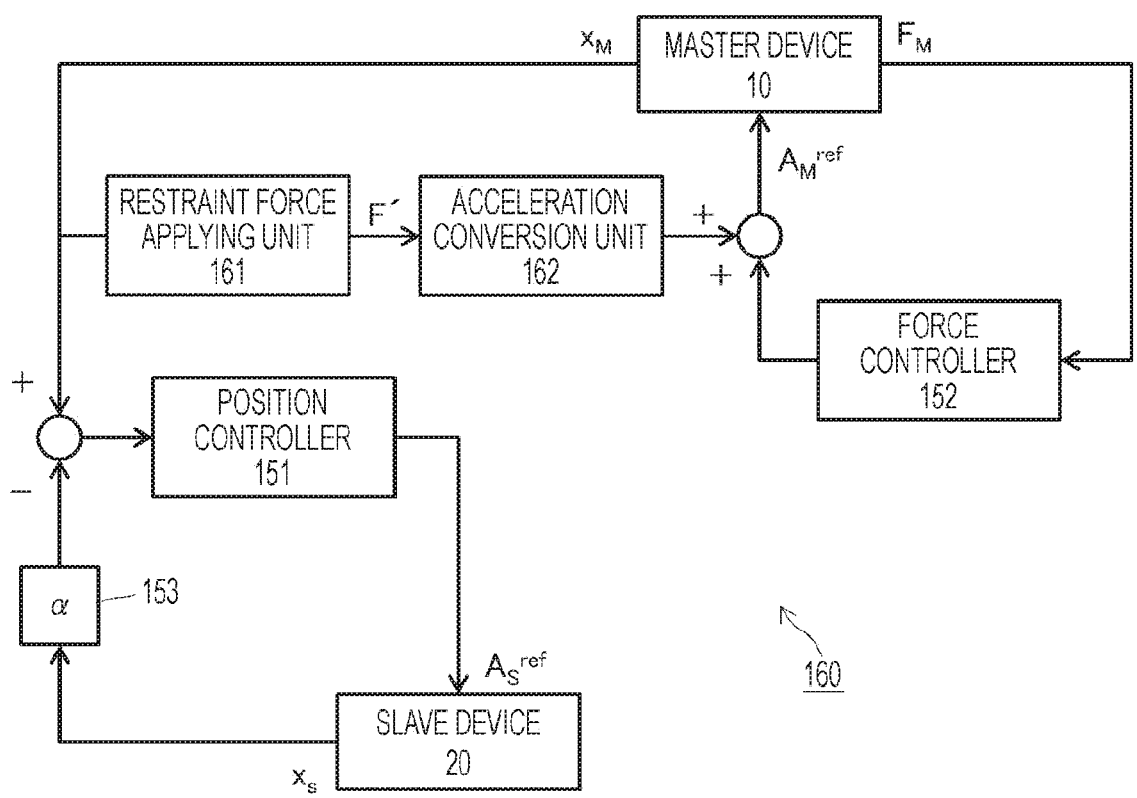
FIG. 16 is a diagram of a functional configuration of a unilateral control system 160 to which the technology diagram herein is applied.

Furthermore, in FIG. 16, a functional configuration of a unilateral control system 160 to which the technology disclosed herein is applied is schematically illustrated. However, a component same as that in the system 150 illustrated in FIG. 15 is denoted with the same reference number. The illustrated system 160 has a configuration in which the restraint force is converted into the acceleration dimension and is applied to the unilateral control system, and the place where the restraint force is fed back is different from that of the system 130 illustrated in FIG. 15.

A restraint force applying unit 161 calculates the restraint force F according to the difference between the current position and posture $X_M$ of the master device 10 and the restraint position/posture reference value $X^{ref}$ and further converts the restraint force F into the coordinate system that actually restrains the master device 10 so as to obtain the restraint force F'. Next, an acceleration conversion unit 162 converts the calculated restraint force F' into an acceleration dimension signal.

Then, an acceleration signal $A_M^{ref}$ obtained by applying an acceleration component caused by the restraint force F' in addition to the acceleration reference signal supplied from the force controller 52 is supplied to the master device 10.

Note that the restraint force F' output by the restraint force applying unit 161 is a virtual force that allows the master device 10 (or grip portion 220 thereof) to move only in a certain direction (for example, arbitrary translational or rotational direction). However, for example, the restraint force F' can be calculated according to the processing procedure illustrated in FIG. 8. However, the restraint force applying unit 161 may output the restraint force for keeping the grip portion 220 at the current position and posture (that is, restraining all the six degrees of freedom) in a state where the grip portion 220 is not held. In the latter case, for example, the restraint force can be calculated according to the processing procedure illustrated in FIG. 11.

So far, an exemplary system configuration in which the restraint force is applied to the master device 10 and the slave device 20 in an arbitrary translational or rotational direction (including all the six degrees of freedom) is indicated. As an application example, a system can be configured to apply a movable range limiting force so that at least one of the master device 10 or the slave device 20 does not move beyond the movable range.

Figure 17:
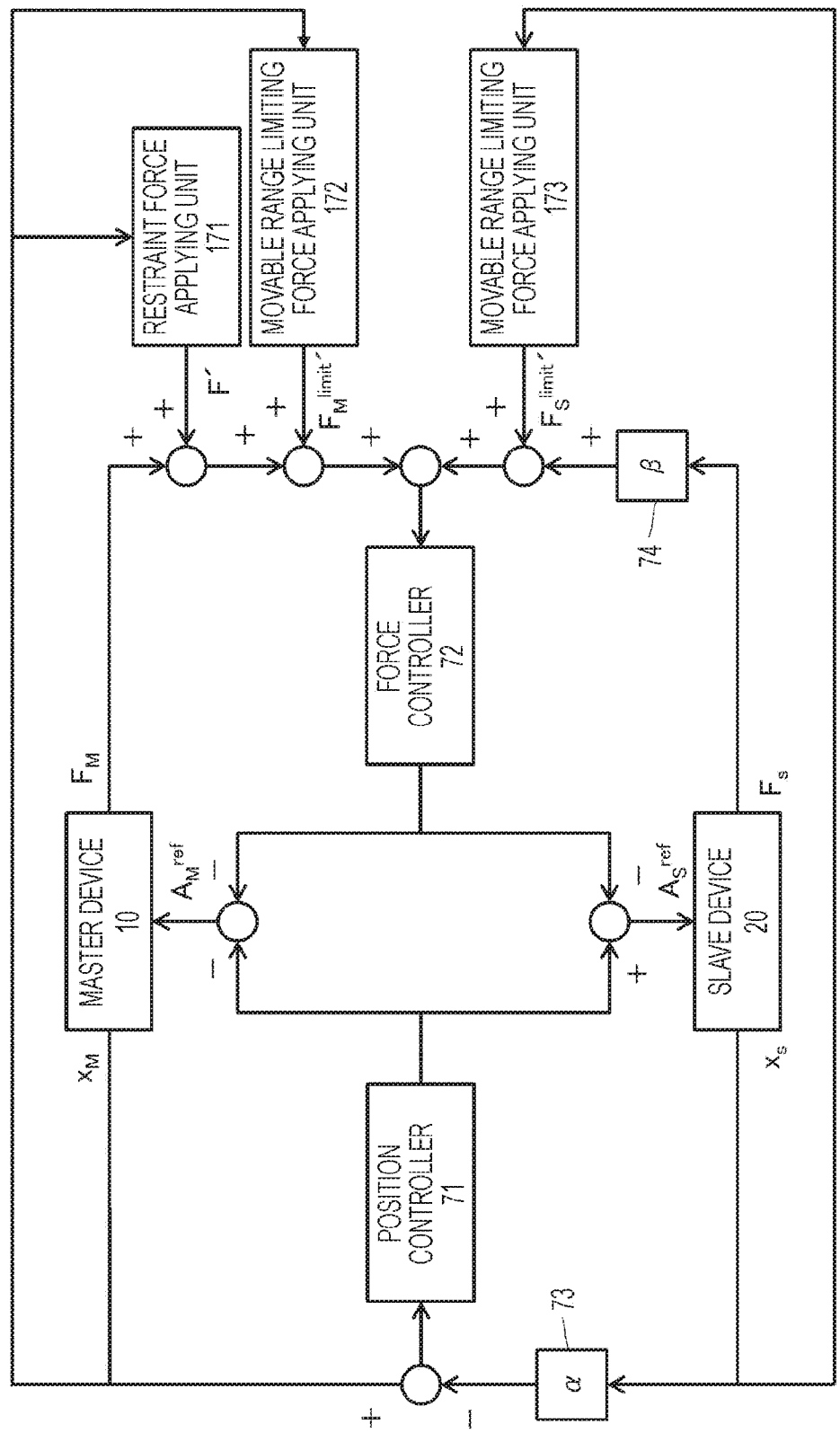
FIG. 17 is a diagram of an exemplary configuration of a bilateral control system 1200 that feeds back a movable range limiting force so that the master device 10 and the slave device 20 do not move beyond a movable range.

In FIG. 17, an exemplary configuration of a bilateral control system 170 is illustrated in which the restraint force is fed back to the bilateral control system of the master-slave robot and the movable range limiting force is fed back so that the master device 10 and the slave device 20 do not move beyond the movable range. However, a component same as that in the system 70 illustrated in FIG. 7 is denoted with the same reference number.

A restraint force applying unit 171 calculates the restraint force F according to the difference between the current position and posture $X_M$ of the master device 10 and the restraint position/posture reference value $X^{ref}$ and further converts the restraint force F into the coordinate system that actually restrains the master device 10 so as to obtain the restraint force F'. The restraint force F' is a virtual force that allows the master device 10 (or grip portion 220 thereof) to move only in a certain direction (for example, arbitrary translational or rotational direction). However, for example, the restraint force F' can be calculated according to the processing procedure illustrated in FIG. 8.

In a case where the current position or posture of the master device 10 moves beyond the movable range of the master device 10, a movable range limiting force applying unit 172 calculates a movable range limiting force $F_M^{limit}$ relative to the master device 10 according to a difference between the current position and posture $X_M$ of the master device 10 and a movable range reference value $X_M^{limit,ref}$ of the master device 10, further converts the calculated force into a coordinate system that actually restrains the master device 10, and obtains a movable range limiting force $F_M^{limit}$. Details of processing for calculating the movable range limiting force $F_M^{limit}$ will be described later.

Furthermore, in a case where the current position or posture of the slave device 20 moves beyond the movable range of the slave device 20, a movable range limiting force applying unit 173 calculates a movable range limiting force $F_S^{limit}$ relative to the slave device 20 according to a difference between the current position and posture $X_M$ of the slave device 20 and a movable range reference value $X_S^{limit,ref}$ of the slave device 20, and further converts the calculated force into a coordinate system that actually restrains the slave device 20, and obtains a movable range limiting force $F_S^{limit}$. Details of processing for calculating the movable range limiting force $F_S^{limit}$ will be described later.

On the basis of a resultant force of the generated force $F_M$ of the master device 10, the restraint force F', the movable range limiting forces $F_M^{limit}$ and $F_S^{limit}$ relative to the master device 10 and the slave device 20, and the generated force $\beta F_S$ of the slave device 20, the force controller 72 outputs an acceleration reference signal to each of the master device 10 and the slave device 20 for driving the devices to a direction to correct this.

Furthermore, on the basis of a positional deviation ($X_M$−$\alpha X_S$) between the master device 10 and the slave device 20, the position controller 71 outputs the acceleration reference signal to each of the master device 10 and the slave device 20 for driving the devices to a direction to correct this.

Then, a signal $A_M^{ref}$ obtained by adding both of the acceleration reference signals respectively supplied from the position controller 71 and the force controller 72 is supplied to the master device 10. Furthermore, a signal $A_S^{ref}$ obtained by adding both of the acceleration reference signals respectively supplied from the position controller 71 and the force controller 72 is supplied to the slave device 20.

There is a case where the grip portion 220 of the master device 10 can be removed and exchanged, a plurality of types of grip portions can be selectively used, and the movable range of the master device 10 changes according to the type of the attached grip portion. In such a case, the movable range limiting force applying unit 172 may recognize an ID of the attached grip portion, acquire a movable range reference value corresponding to the ID, and calculate a movable range limiting force.

Furthermore, there is a case where the surgical instrument to be the end effector of the slave device 20 can be removed and exchanged, a plurality of types of surgical instruments can be selectively used, and the movable range of the slave device 20 changes according to the type of the attached surgical instrument. In such a case, the movable range limiting force applying unit 173 may recognize an ID of the attached surgical instrument, acquire a movable range reference value corresponding to the ID, and calculate a movable range limiting force.

Note that, in FIG. 17, the exemplary system configuration 170 in which both of the restraint force and the movable range limiting force are applied is illustrated. However, a system can be configured to apply only the movable range limiting force. Furthermore, it is possible to configure the system so as to apply only the movable range limiting force of one of the master device 10 or the slave device 20.

Furthermore, a modification can be considered in which the movable range limiting forces output from the movable range limiting force applying units 172 and 173 are converted into the acceleration dimension and applied to the bilateral control system 170 as in the exemplary system configuration illustrated in FIG. 9.

Figure 18:
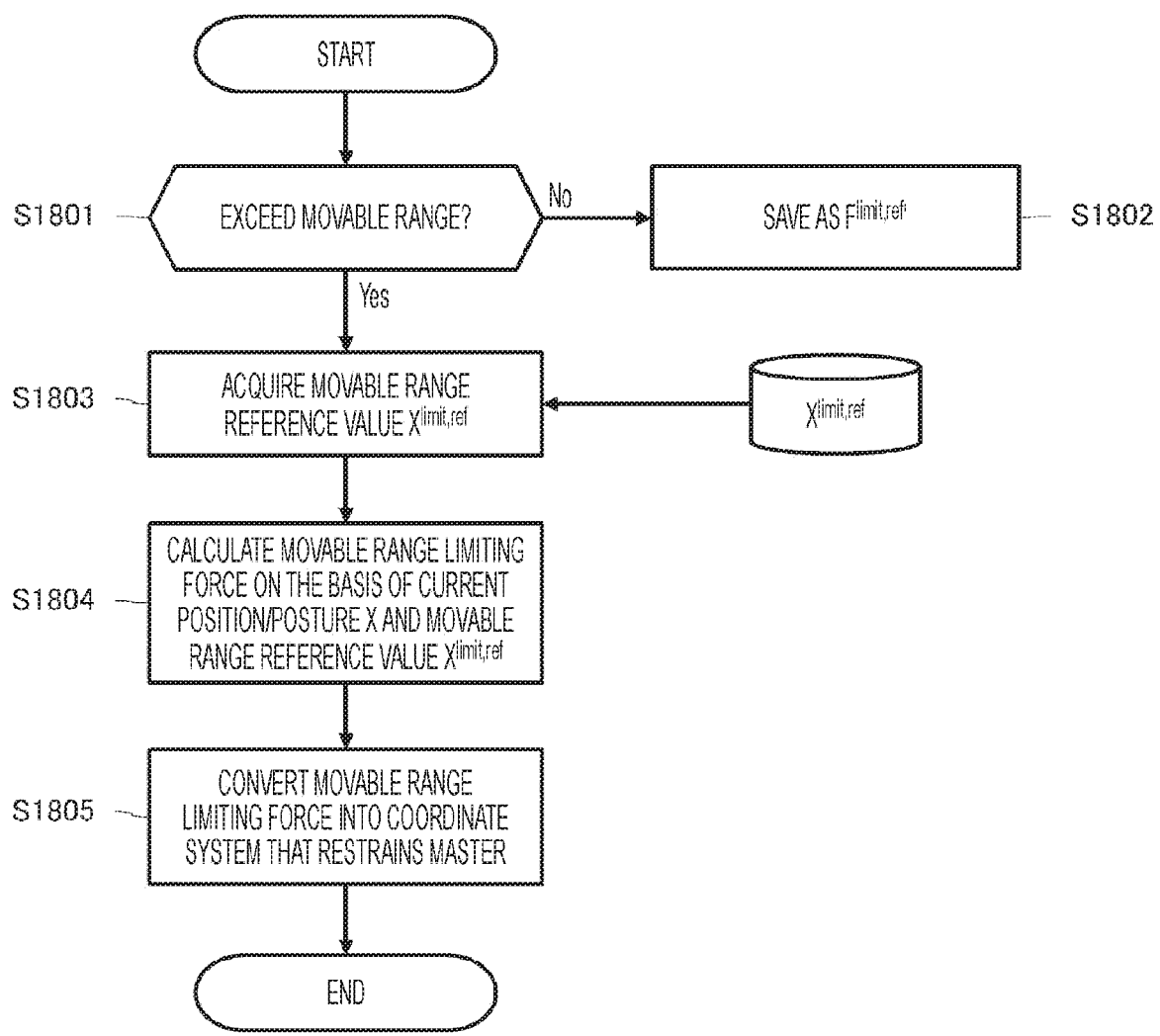
FIG. 18 is a flowchart of a processing procedure for applying a movable range limiting force to a bilateral control system 120.

In FIG. 18, a processing procedure for applying the movable range limiting force, for preventing the master device 10 and the slave device 20 from moving beyond the movable range, to the bilateral control system 120 is illustrated in a form of a flowchart. The illustrated processing procedure can be realized at low cost, for example, as software processing in the control system 30.

First, whether or not the current position or posture of the master device 10 or the slave device 20 is beyond the movable range is checked (step S1801).

For example, on the side of the master device 10, it can be determined whether or not the master device 10 moves beyond the movable range on the basis of a rotation angle at which the encoder disposed in the coupling portion between each of the link portions 231, 232, 233 included in a delta type parallel link and the main body 210 rotates. Furthermore, on the side of the slave device 20, it can be determined whether or not the slave device 20 moves beyond the movable range on the basis of a rotation angle at which the encoder disposed in each of the joint portions 321a to 321f of the arm 320 rotates.

Here, when it is determined that the master device 10 and the slave device 20 do not move beyond the movable range (No in step S1801), it is not necessary to apply the movable range limiting force to the bilateral control system 1200. Therefore, movable range limiting forces $F_M^{limit}=0$ and $F_S^{limit}=0$ are output (step S1802).

On the other hand, when it is determined that at least one of the master device 10 or the slave device 20 moves beyond the movable range (Yes in step S1801), the movable range reference value $X_M^{limit,ref}$ or $X_S^{limit,ref}$ of the device that exceeds the movable range is acquired (step S1803).

Then, the current position and posture $X_M$ of the master device 10 is acquired, and a movable range limiting force $F_M^{limit}$ according to a difference between the current position and posture $X_M$ and a movable range reference value $X_M^{limit,ref}$ is calculated according to the following equation (3) (step S1804). However, in the equation (3), the reference D is a coefficient indicating a gain. Furthermore, the equation (3) derives the movable range limiting force only by a proportional gain. However, it goes without saying that the movable range limiting force can be derived by using other position control method.

[Math. 3]

$$F_M^{limit}=D(X_M^{limit,ref}-X_M) \quad (3)$$

Next, the calculated movable range limiting force $F_M^{limit}$ is converted into a coordinate system that actually restrains the master device 10 according to the following equation (4) (step S1805) and is output as a virtual restraint force $F_M^{limit'}$.

[Math. 4]

$$F_M^{limit'}=\text{Trans}(F_M^{limit}) \quad (4)$$

Alternatively, in step S1804, the current position and posture $X_S$ of the slave device 20 is acquired, and a movable range limiting force $F_S^{limit}$ according to a difference between the current position and posture $X_S$ and a movable range reference value $X_S^{limit,ref}$ is calculated according to the following equation (5) (step S1804). Then, in step S1805, the calculated movable range limiting force $F_S^{limit}$ is converted into a coordinate system that actually restrains the slave device 20 according to the following equation (6) and is output as a virtual restraint force $F_S^{limit'}$.

[Math. 5]

$$F_S^{limit}=D(X_S^{limit,ref}-X_S) \quad (5)$$

[Math. 6]

$$F_S^{limit'}=\text{Trans}(F_S^{limit}) \quad (6)$$

According to the system configuration 170 illustrated in FIG. 17, when the user remotely operates the slave device 20 by using the grip portion 220 from the master device 10, the restraint force F' that restrains the operation of the grip portion 220 in an arbitrary translational or rotational direction and the movable range limiting force $F^{limit'}$ that prevents the master device 10 and the slave device 20 from moving out of the movable range act. Therefore, the user can improve operation accuracy by receiving support or assistance of the restraint force in a range in which the master device 10 and the slave device 20 do not move out of the movable range, and the task processing time (treatment time and the like) can be shortened.

Subsequently, an operation UI and a presentation UI of the bilateral control system will be described.

As input means on the side of the master device 10 that can be used by the user, the jog dial and the tact switch provided on the grip portion, the foot pedal switch installed at the foot, and the like can be exemplified. As already known, continuous input is possible by using the jog dial. On the other hand, the tact switch and the foot pedal switch can input zero or one according to on/off of the switches.

Furthermore, in a case where the user desires to apply the restraint force to the operation by using the grip portion 220 in an arbitrary translational or rotational direction when the slave device 20 is remotely operated by the side of the master device 10, for example, it is necessary to designate parameters as indicated in (a) to (b) below.

(a) Type of restraint force (translation or rotation)

(b) Axial direction to which restraint force is applied (x, y, z)

(c) Degree of freedom to which restraint force is applied (one to six degrees of freedom)

(d) Coordinate system to which restraint force is applied (global coordinate system or local coordinate system (of slave device 20))

The user can select an item from among the above items (a) to (d) by using any one of the jog dial, the tact switch, and the foot pedal switch and can further switch the selected input means.

In a case where the robot system 1 is applied to, for example, a surgical system, it is extremely difficult for the user who is an operator to perform a complicated input operation during surgery. Therefore, it is preferable to employ a simple input method, for example, by serially arranging a plurality of options including combinations of the items (a) and (b), and the like so as to select the option by passing the options in order each time when the jog dial is rotated by a predetermined angle or so as to sequentially select two alternative options such as a coordinate system each time when the tact switch or the foot pedal switch is pressed.

Figure 19:
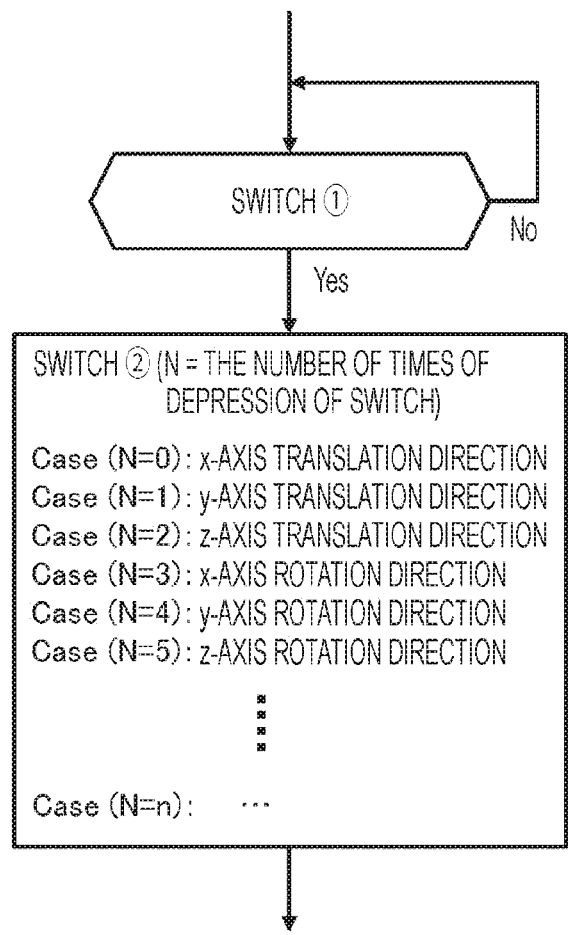
FIG. 19 is a flowchart of a processing procedure for switching a type of the restraint force and the like to be applied to the bilateral control system in response to an UI operation by a user.

In FIG. 19, a processing procedure for sequentially switching the type of restraint force to be applied to the bilateral control system, the axial direction of the restraint force, the degree of freedom to which the restraint force is applied, the coordinate system, and the like each time when the user performs a UI operation is illustrated in a form of a flowchart.

For example, in the bilateral control system 70 illustrated in FIG. 7, the restraint force applying unit 75 calculates the restraint force on the basis of the type of the restraint force, the axial direction of the restraint force, the degree of freedom to which the restraint force is applied, and the coordinate system that are set according to the above processing procedure and feeds back the calculated restraint force to a control system.

Furthermore, when the type of the restraint force, the axial direction of the restraint force, the degree of freedom to which the restraint force is applied, and the like are switched in response to the UI operation by the user, it is preferable that, for example, a current selection state regarding the items (a) to (d) above on a screen of the monitor 260 so as to allow the user to confirm the selection state.

Figure 20:
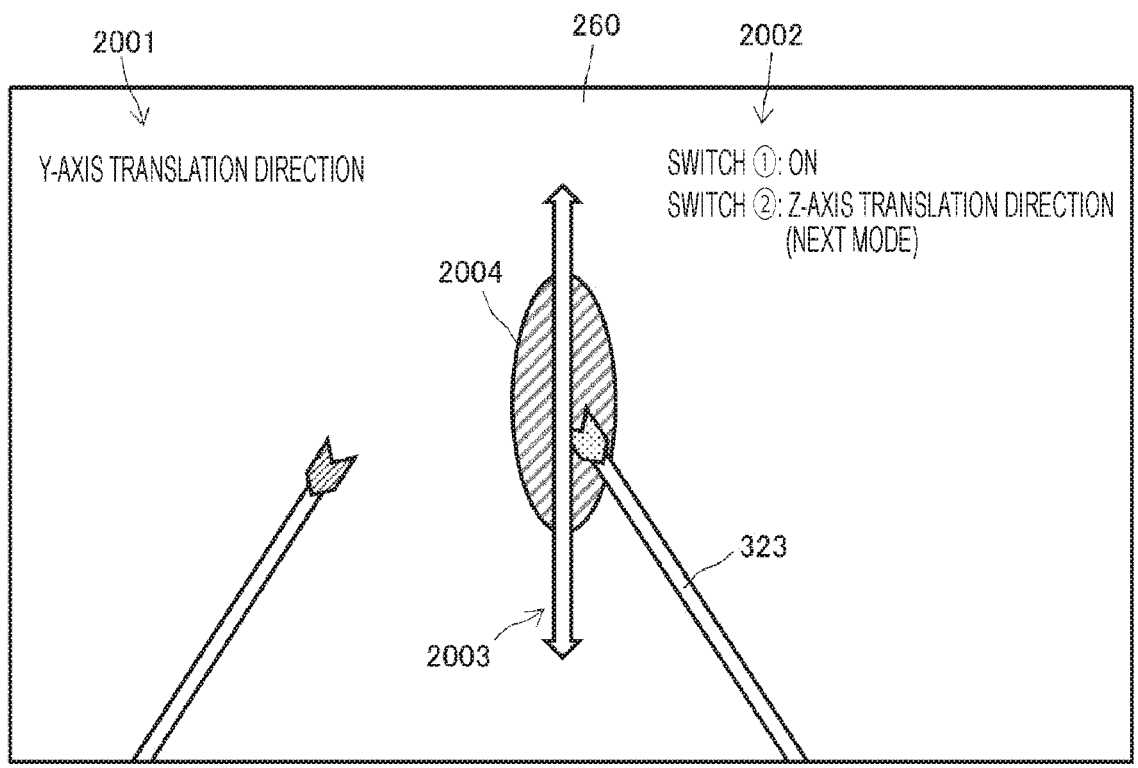
FIG. 20 is a diagram of an example in which a selection state regarding the restraint force is displayed on a screen.

In FIG. 20, a state where the selection state regarding the restraint force is displayed on the screen of the monitor 260 is illustrated. In the illustrated example, as indicated by a reference number 2001, the selected type and axial direction of the restraint force are displayed on the screen. Furthermore, as indicated by a reference number 2002, a switch operation method is also displayed on the screen. Note that a name of the axial direction displayed on the screen may be another name such as "screen vertical direction", "screen depth direction", or the like.

Moreover, as indicated by a reference number 2003, an arrow indicating a current movable direction is displayed. If the movable direction 2003 is displayed so as to overlap with an image of the forceps 323 that is a remote operation target, the user can easily grasp the movable direction 2003. However, the front end of the forceps 323 often has contact with an affected part 2004. Therefore, there is a possibility that the video 2003 indicating the movable direction overlaps with the affected part 2004, that it is difficult to see the affected part 2004, and the video 2003 interferes with the treatment. Therefore, it is preferable that the movable direction 2003 do not disturb the observation of the affected part 2004, for example, by displaying the movable direction 2003 only for a predetermined period from the time of switching the selection, semi-transparently displaying the movable direction 2003, displaying the movable direction 2003 at a place apart from the front end of the forceps 323, displaying the movable direction 2003 in the periphery of the screen 260, and the like.

Figure 21:
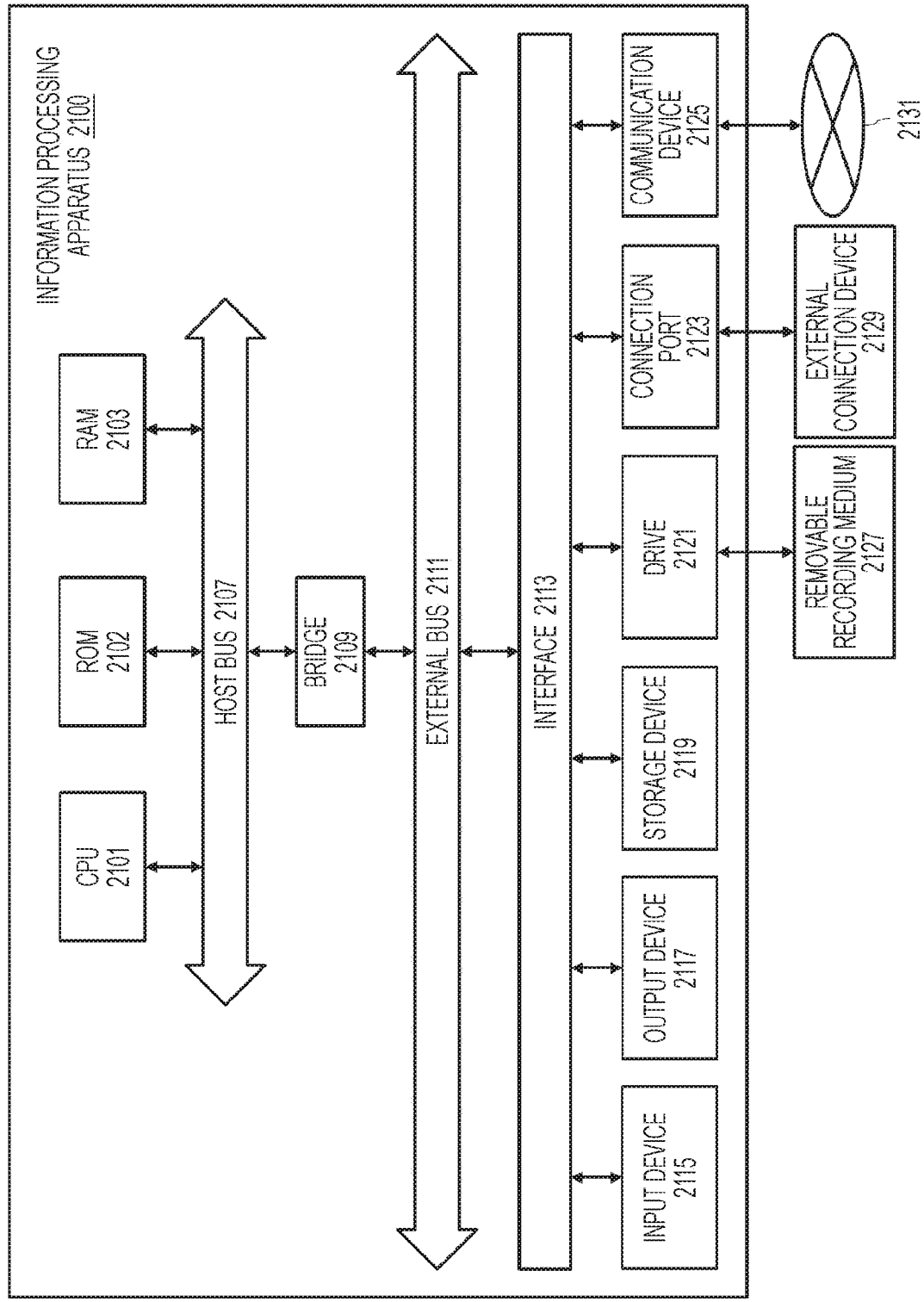
FIG. 21 is a diagram of a hardware configuration of an information processing apparatus 2100 included in a control system 30.

In FIG. 21, a hardware configuration of an information processing apparatus 2100 that can behave as the control system 30 in the robot system 1 illustrated in FIG. 1 is illustrated.

The illustrated information processing apparatus 2100 mainly includes a CPU 2101, a read only memory (ROM) 2103, and a random access memory (RAM) 2105 and further includes a host bus 2107, a bridge 2109, an external bus 2111, an interface 2113, an input device 2115, an output device 2117, a storage device 2119, a drive 2121, a connection port 2123, and a communication device 2125.

The CPU 2101 functions as a calculation processing device and a control device and controls all or a part of behaviors in the information processing apparatus 2100 according to various programs recorded in the ROM 2103, the RAM 2105, the storage device 2119, or a removable recording medium 2127. The ROM 2103 stores a program, a calculation parameter, and the like used by the CPU 2101 in a nonvolatile manner. The RAM 2105 temporarily stores a program used by the CPU 2101, a parameter that appropriately changes during execution of the program, and the like. These are connected to each other by the host bus 2107 including an internal bus such as a CPU bus. Note that the function of the control system 30 in the robot system 1 illustrated in FIG. 1 may be realized, for example, by executing a predetermined program by the CPU 2101.

The host bus 2107 is connected to the external bus 2111 such as a peripheral component interconnect (PCI) bus via the bridge 2109. Furthermore, the external bus 2111 is connected to the input device 2115, the output device 2117, the storage device 2119, the drive 2121, the connection port 2123, and the communication device 2125 via the interface 2113.

The input device 2115 includes, for example, an operation device that is operated by a user such as a mouse, a keyboard, a touch panel, a button, a switch, a lever, a pedal, and the like. Furthermore, the input device 2115 may be, for example, a remote controller (so-called remote controller) using infrared rays and other radio waves or may be an external connection device 2129 such as a mobile phone, a smartphone, a personal digital assistant (PDA), and the like corresponding to the operation of the information processing apparatus 2100. Moreover, for example, the input device 2115 includes an input control circuit and the like that generates an input signal on the basis of information input by the user by using the above operation devices and outputs the signal to the CPU 2101. The user of the information processing apparatus 2100 can input various data and instruct a processing behavior to the information processing apparatus 2100 by operating the input device 2115.

The output device 2117 includes a device that can visually or audibly notifies the user of the acquired information. As such a device, a display device such as a CRT display device, a liquid crystal display device, a plasma display device, an EL display device, a lamp, and the like, an audio output device such as a speaker, a headphone, or the like, a printer device, and the like are exemplified. The output device 2117, for example, outputs results obtained by various processing executed by the information processing apparatus 2100. Specifically, the display device displays the results obtained by various processing executed by the information processing apparatus 2100 as a text or an image. The audio output device converts an audio signal including reproduced audio data, acoustic data, and the like into an analog signal and outputs sound. Note that the monitor 260 included in the master device 10 may be realized, for example, by the output device 2117.

The storage device 2119 is a device for data storage that is configured as an example of a storage unit of the information processing apparatus 2100. The storage device 2119 includes, for example, a magnetic storage unit device such as a hard disk drive (HDD), a semiconductor storage device, an optical storage device, a magneto-optical storage device, or the like. The storage device 2119 stores a program executed by the CPU 2101, various data, and the like.

The drive 2121 is a reader/writer for a recording medium and is built in or externally attached to the information processing apparatus 2100. The drive 2121 reads information recorded in the removable recording medium 2127 such as the attached magnetic disk, optical disk, magneto-optical disk, semiconductor memory, and the like and outputs the information to the RAM 2105 and the like. Furthermore, the drive 2121 can write a record to the removable recording medium 2127 such as the attached magnetic disk, optical disk, magneto-optical disk, semiconductor memory, or the like. The removable recording medium 2127 is, for example, DVD media, or HD-DVD media, or Blu-ray (registered trademark) media. Furthermore, the removable recording medium 2127 may be a CompactFlash (CF) (registered trademark), a flash memory, a secure digital (SD) memory card, or the like. Furthermore, the removable recording medium 2127 may be, for example, an integrated circuit (IC) card, an electronic apparatus, or the like on which a non-contact IC chip is mounted.

The connection port 2123 is a port that is directly connected to the information processing apparatus 2100. Examples of the connection port 2123 include a universal serial bus (USB) port, an IEEE1394 port, a small computer system interface (SCSI) port, and the like. Another examples of the connection port 2123 include an RS-232C port, an optical audio terminal, a high-definition multimedia interface (HDMI) (registered trademark) port, and the like. By connecting the external connection device 2129 to the connection port 2123, the information processing apparatus 2100 directly acquires various data from the external connection device 2129 and provides various data to the external connection device 2129.

The communication device 2125 is a communication interface including, for example, a communication device used to be connected to a communication network (network) 2131 and the like. The communication device 2125 is, for example, a communication card for a wired or wireless local area network (LAN), the Bluetooth (registered trademark), and a wireless USB (WUSB), and the like. Furthermore, the communication device 2125 may be a router for optical communication, a router for asymmetric digital subscriber line (ADSL), a modem for various communication, and the like. For example, the communication device 2125 can exchange a transmission signal with the Internet and other communication devices according to a predetermined protocol, for example, TCP/IP and the like. Furthermore, the communication network 2131 connected to the communication device 2125 includes a network that is wiredly or wirelessly connected and the like and may be, for example, the Internet, a home LAN, infrared communication, radio wave communication, satellite communication, or the like.

The example of the hardware configuration of the information processing apparatus 2100 that can realize the function of the control system 30 in the robot system 1 according to the present embodiment has been described above. Each component may be formed by using a general-purpose member or hardware specialized to the function of each component. Therefore, it is possible to appropriately change the hardware configuration to be used according to a technical level at the time of carrying out the present embodiment. Note that, although illustration is omitted in FIG. 21, it is assumed to naturally include various configurations corresponding to the information processing apparatus 2100 included in the control system 30 according to the present embodiment.

Note that it is possible to produce a computer program to realize each function of the information processing apparatus 2100 included in the control system 30 according to the present embodiment described above and implement the produced program on a personal computer and the like. Furthermore, a computer-readable recording medium storing such a computer program can be provided. The recording medium is, for example, a magnetic disk, an optical disk, a magneto-optical disk, a flash memory, and the like. Furthermore, the computer program may be distributed, for example, via a network, without using the recording medium. Furthermore, the number of computers that execute the computer program is not particularly limited. For example, the plurality of computers (for example, a plurality of servers) may execute the computer program in cooperation with each other. Note that a single computer or a system in which a plurality of computers performs in cooperation with each other are referred to as a "computer system".

INDUSTRIAL APPLICABILITY

The technology disclosed herein has been described above in detail with reference to the specific embodiment. However, it is obvious that those skilled in the art can amend and substitute the embodiment without departing from the scope of the technology disclosed herein.

The technology disclosed herein can be applied to the master-slave system that is driven by various control systems including the bilateral control system and the unilateral control system. Furthermore, an application range of the technology disclosed herein is not limited to a configuration of a specific robot (plant).

In a word, the technology disclosed herein has been described as an example, and the described matter in the present specification should not be restrictively interpreted. Claims should be considered in order to determine the scope of the technology disclosed herein.

Note that the technology disclosed herein can have the following configuration.

(1) A control device that controls an operation of a master-slave system, including:
    a control unit configured to apply, to a control system of the master-slave system, a restraint force corresponding to an operation in a desired translational or rotational direction by the master.

(2) The control device according to (1), in which
    the control unit applies, to the control system, the restraint force according to a difference between a current position or posture of the master and a reference value of a position or posture to be restrained.

(2-1) The control device according to (2), in which
a position or posture of the master one or a predetermined control cycle before is held as the reference value.
(3) The control device according to (1) or (2), in which the control unit converts the restraint force into an acceleration dimension and applies the converted force to the control system.
(4) The control device according to (1) or (2), in which the control unit simultaneously applies, to the control system, restraint forces in a plurality of translational or rotational directions.
(5) The control device according to (1) or (2), in which the control unit applies the restraint force that restrains all degrees of freedom of the master to the control system when the master is out of an operation by a user.
(6) The control device according to any one of (1) to (5), in which
the control unit further applies, to the control system, a movable range limiting force that limits a position and a posture of the master or the slave so as not to move beyond a predetermined movable range.
(7) The control device according to any one of (1) to (6), in which
the control unit controls the restraint force to be applied to the control system according to an operation of a user on an input unit included in the master.
(8) The control device according to (7), in which
the control unit switches, according to the operation of the user on the input unit, a combination of at least one or two or more of a type of the restraint force, an axial direction to which the restraint force is applied, a degree of freedom to which the restraint force is applied, or a coordinate system to which the restraint force is applied.
(9) The control device according to (7) or (8), in which
the control unit further controls a display output of a situation selected according to the operation of the user on the input unit.
(10) The control device according to any one of (1) to (9), in which
the control system controls the master-slave system by a bilateral control method.
(11) The control device according to any one of (1) to (9), in which
the control system controls the master-slave system by a unilateral control method.
(12) A control method for controlling an operation of a master-slave system, including:
a control step of applying, to a control system of the master-slave system, a restraint force corresponding to an operation in a desired translational or rotational direction by the master.
(13) A master-slave system including:
a master;
a slave; and
a control unit configured to control an operation of the slave by the master, in which
the control unit applies a restraint force corresponding to an operation in a desired translational or rotational direction by the master.
(14) The master-slave system according to (13), in which
the master includes a support arm unit having a parallel link structure and a grip portion disposed on a side of a distal end of the support arm unit.
(15) The master-slave system according to (13) or (14), in which
the slave includes a detection unit that detects an external force, and the master includes a force presentation unit that presents a force based on a detection result by the detection unit.
(16) The master-slave system according to any one of (13) to (15), in which
the slave includes a multi-link arm.
(17) The master-slave system according to (16), in which
the slave includes a medical unit at a front end of the multi-link arm.

REFERENCE SIGNS LIST

1 Robot system
10 Master device
11 Input unit
12 Force presentation unit
20 Slave device
21 Drive unit
22 State detection unit
30 Control system
40 Bilateral control system (position-symmetric type)
41 Position controller
42 Scaler
50 Bilateral control system (force-feedback type)
51 Position controller
52 Force controller
53, 54 Scaler
60 Bilateral control system (4CH-type)
61 Position controller
62 Force controller
63, 64 Scaler
70 Bilateral control system (4CH-type)
71 Position controller
72 Force controller
73, 74 Scaler
75 Restraint force applying unit
90 Bilateral control system (4CH-type)
91 Restraint force applying unit
92 Acceleration conversion unit
100 Bilateral control system (4CH-type)
101 State detection unit
102 Restraint force applying unit
120 Bilateral control system (position-symmetric type)
121 Restraint force applying unit
122 Acceleration conversion unit
130 Bilateral control system (force-feedback type)
131 Restraint force applying unit
140 Bilateral control system (force-feedback type)
141 Restraint force applying unit
142 Acceleration conversion unit
150 Unilateral control system
151 Position controller
152 Force controller
153 Scaler
154 Restraint force applying unit
160 Unilateral control system
161 Restraint force applying unit
162 Acceleration conversion unit
170 Bilateral control system (4CH-type)
171 Restraint force applying unit
172, 173 Movable range limiting force applying unit
210 Main body
220 Grip portion
231 to 233 Link portion 241 to 243 Motor
250 Support base
260 Monitor
300 Support arm device
310 Base
320 Arm
321a to 321f Joint portion
322a to 322d Link
323 Forceps
329 Holding unit
2100 Information processing apparatus
2101 CPU
2103 ROM
2105 RAM
2107 Host bus
2109 Bridge
2111 External bus
2113 Interface
2115 Input device
2117 Output device
2119 Storage device
2121 Drive
2123 Connection port
2125 Communication device

The invention claimed is:

1. A control device, comprising:
a central processing unit (CPU) configured to:
apply, to a control system of a master-slave system, a restraint force corresponding to an operation in one of a translational direction or a rotational direction by a master;
apply, to the control system of the master-slave system, a movable range limiting force that limits a position and a posture of one of the master or a slave so as not to move beyond a determined movable range of the one of the master or the slave, wherein
the determined movable range of the master is changeable based on a type of a grip portion attached to the master, and
the determined movable range of the slave is changeable based on a type of a medical instrument attached to the slave; and
output, to each of the master and the slave, an acceleration reference signal based on a generated force of the master, the restraint force, and a generated force of the slave.

2. The control device according to claim 1, wherein the CPU is further configured to apply, to the control system, the restraint force based on a difference between a current position or a current posture of the master and a reference value of a position or a posture to be restrained.

3. The control device according to claim 1, wherein the CPU is further configured to:
convert the restraint force into an acceleration dimension; and
apply the converted restraint force to the control system.

4. The control device according to claim 1, wherein the CPU is further configured to apply, to the control system, a plurality of restraint forces, including the restraint force, in a plurality of translational or rotational directions.

5. The control device according to claim 1, wherein the CPU is further configured to apply, to the control system, the restraint force that restrains all degrees of freedom of the master in a case the master is out of the operation by a user.

6. The control device according to claim 1, wherein the CPU is further configured to control the restraint force to be applied to the control system based on the operation of a user on an input unit included in the master.

7. The control device according to claim 6, wherein the CPU is further configured to switch, according to the operation of the user on the input unit, at least one of a type of the restraint force, an axial direction to which the restraint force is applied, a degree of freedom to which the restraint force is applied, or a coordinate system to which the restraint force is applied.

8. The control device according to claim 6, wherein the CPU is further configured to control display of a situation selected according to the operation of the user on the input unit.

9. The control device according to claim 1, wherein the CPU is further configured to control the master-slave system by a bilateral control method.

10. The control device according to claim 1, wherein the CPU is further configured to control the master-slave system by a unilateral control method.

11. A control method, comprising:
applying, to a control system of a master-slave system, a restraint force corresponding to an operation in one of a translational direction or a rotational direction by a master;
applying, to the control system of the master-slave system, a movable range limiting force that limits a position and a posture of one of the master or a slave so as not to move beyond a determined movable range of the one of the master or the slave, wherein
the determined movable range of the master is changeable based on a type of a grip portion attached to the master, and
the determined movable range of the slave is changeable based on a type of a medical instrument attached to the slave; and
outputting, to each of the master and the slave, an acceleration reference signal based on a generated force of the master, the restraint force, and a generated force of the slave.

12. A master-slave system, comprising:
a master;
a slave; and
a central processing unit (CPU) configured to:
control an operation of the slave by the master;
apply, to the master-slave system, a restraint force corresponding to an operation in one of a translational direction or a rotational direction by the master;
apply, to the master-slave system, a movable range limiting force that limits a position and a posture of one of the master or the slave so as not to move beyond a determined movable range of the one of the master or the slave, wherein
the determined movable range of the master is changeable based on a type of a grip portion attached to the master, and
the determined movable range of the slave is changeable based on a type of a medical instrument attached to the slave; and
output, to each of the master and the slave, an acceleration reference signal based on a generated force of the master, the restraint force, and a generated force of the slave.

13. The master-slave system according to claim 12, wherein
the master includes a support arm unit having a parallel link structure, and the grip portion is on a side of a distal end of the support arm unit.

14. The master-slave system according to claim 12, wherein
the slave includes a detection unit configured to detect an external force acting on the medical instrument, and
the master includes a force presentation unit configured to present a force based on the detected external force.

15. The master-slave system according to claim 12, wherein the slave includes a multi-link arm.

16. The master-slave system according to claim 15, wherein the medical instrument is at a front end of the multi-link arm.

* * * * *